(12) United States Patent
Berman et al.

(10) Patent No.: US 10,360,368 B2
(45) Date of Patent: Jul. 23, 2019

(54) APPLICATION INTERFACE AND DISPLAY CONTROL IN AN ANALYTE MONITORING ENVIRONMENT

(71) Applicant: ABBOTT DIABETES CARE INC., Alameda, CA (US)

(72) Inventors: Glenn Berman, Alameda, CA (US); Nathan Crouther, San Francisco, CA (US); Michael R. Love, Pleasanton, CA (US); Mark Sloan, Redwood City, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 0 days.

(21) Appl. No.: 14/575,950

(22) Filed: Dec. 18, 2014

(65) Prior Publication Data
US 2015/0205947 A1    Jul. 23, 2015

Related U.S. Application Data

(60) Provisional application No. 61/921,375, filed on Dec. 27, 2013.

(51) Int. Cl.
| | |
|---|---|
| *G06F 21/44* | (2013.01) |
| *A61B 5/00* | (2006.01) |
| *A61B 5/145* | (2006.01) |
| *G16H 40/63* | (2018.01) |
| *H04W 4/80* | (2018.01) |

(Continued)

(52) U.S. Cl.
CPC ............ *G06F 21/44* (2013.01); *A61B 5/0031* (2013.01); *A61B 5/14532* (2013.01); *G16H 40/63* (2018.01); *A61B 5/150847* (2013.01); *G06F 19/3418* (2013.01); *H04L 67/12* (2013.01); *H04W 4/80* (2018.02)

(58) Field of Classification Search
CPC ........................................................ G06F 21/44
USPC ............................................. 726/16; 600/309
See application file for complete search history.

(56) References Cited

U.S. PATENT DOCUMENTS

| | | | | |
|---|---|---|---|---|
| 5,837,546 | A | * | 11/1998 | Allen .................. G01N 33/5438 422/403 |
| 6,377,894 | B1 | | 4/2002 | Deweese et al. |

(Continued)

FOREIGN PATENT DOCUMENTS

| | | |
|---|---|---|
| EP | 14873183.9 | 7/2017 |
| WO | WO 2010/021084 A1 | 10/2010 |

(Continued)

OTHER PUBLICATIONS

Archibong, "A Mobile Phone-based approach to detection of hemolysis", Aug. 16, 2016, Biosensors and Bioelectronic, pp. 204-209 (Year: 2016).*

(Continued)

*Primary Examiner* — Kenneth W Chang
*Assistant Examiner* — Gregory A Lane
(74) *Attorney, Agent, or Firm* — One LLP

(57) ABSTRACT

Systems, devices, and methods are provided for the control of interfacing between applications that facilitate the monitoring of diabetes running on a mobile device, including the authentication of a third party user interface application by a sensor interface application. Control of the display of current analyte levels and critical events is also provided.

28 Claims, 7 Drawing Sheets

(51) Int. Cl.
*G06F 19/00* (2018.01)
*A61B 5/15* (2006.01)
*H04L 29/08* (2006.01)

(56) References Cited

U.S. PATENT DOCUMENTS

| | | | |
|---|---|---|---|
| 6,616,819 B1 | 9/2003 | Liamos et al. | |
| 6,736,957 B1 | 5/2004 | Forrow et al. | |
| 7,418,285 B2 | 8/2008 | Ghesquiere et al. | |
| 7,501,053 B2 | 3/2009 | Karinka et al. | |
| 7,749,740 B2 | 7/2010 | Eiteman et al. | |
| 7,754,093 B2 | 7/2010 | Forrow et al. | |
| 2001/0049263 A1* | 12/2001 | Zhang | G06F 8/65 455/67.11 |
| 2003/0036683 A1* | 2/2003 | Kehr | G06F 19/325 600/300 |
| 2003/0212601 A1* | 11/2003 | Silva | G06Q 20/02 705/17 |
| 2004/0078219 A1* | 4/2004 | Kaylor | G06Q 50/22 705/2 |
| 2004/0118704 A1 | 6/2004 | Wang et al. | |
| 2004/0172301 A1 | 9/2004 | Mihai et al. | |
| 2006/0091006 A1 | 5/2006 | Wang et al. | |
| 2006/0258917 A1* | 11/2006 | Burd | A61B 5/6887 600/309 |
| 2006/0294027 A1* | 12/2006 | Jain | G06Q 40/04 705/400 |
| 2008/0066305 A1 | 3/2008 | Wang et al. | |
| 2008/0104104 A1* | 5/2008 | Nolan | G06F 17/30011 |
| 2008/0256643 A1* | 10/2008 | Jones | G06F 21/629 726/27 |
| 2008/0267823 A1 | 10/2008 | Wang et al. | |
| 2009/0105636 A1* | 4/2009 | Hayter | A61M 5/1723 604/66 |
| 2010/0081905 A1 | 4/2010 | Bommakanti et al. | |
| 2010/0094110 A1 | 4/2010 | Heller et al. | |
| 2010/0094111 A1 | 4/2010 | Heller et al. | |
| 2010/0094112 A1 | 4/2010 | Heller et al. | |
| 2010/0230285 A1 | 9/2010 | Hoss et al. | |
| 2010/0324392 A1 | 12/2010 | Yee et al. | |
| 2011/0082484 A1 | 4/2011 | Saravia et al. | |
| 2011/0106126 A1 | 5/2011 | Love et al. | |
| 2011/0184264 A1 | 7/2011 | Galasso et al. | |
| 2011/0190603 A1 | 8/2011 | Stafford | |
| 2011/0191044 A1 | 8/2011 | Stafford | |
| 2011/0193704 A1 | 8/2011 | Harper et al. | |
| 2011/0213225 A1* | 9/2011 | Bernstein | G06Q 50/22 600/309 |
| 2011/0319729 A1 | 12/2011 | Donnay et al. | |
| 2012/0054841 A1* | 3/2012 | Schultz | G06F 21/44 726/6 |
| 2012/0123227 A1* | 5/2012 | Sun | A61B 5/14532 600/309 |
| 2012/0150005 A1 | 6/2012 | Noss et al. | |
| 2012/0179908 A1* | 7/2012 | Duma | G06F 19/323 713/165 |
| 2012/0197222 A1 | 8/2012 | Donnay et al. | |
| 2012/0228134 A1 | 9/2012 | Simpson et al. | |
| 2012/0232520 A1* | 9/2012 | Sloan | A61B 5/14532 604/504 |
| 2012/0245447 A1 | 9/2012 | Karan et al. | |
| 2012/0260323 A1* | 10/2012 | San Vicente | A61B 5/002 726/6 |
| 2013/0282403 A1 | 10/2013 | Hayter et al. | |

FOREIGN PATENT DOCUMENTS

WO PCT/US2014/71296 3/2015
WO WO 6/2016
PCT/US2014/071296

OTHER PUBLICATIONS

Summers, N., "Glooko updates its diabetes-management iOS app with automatic blood glucose averages", 2013, retrieved from https://thenextweb.com/apps/2013/03/05/glooko-updates-its-ios-app-with-automatic-blood-glucose-averages-to-help-diabetics-benchmark-against-previous-weeks/#.tnw_2GQfl08t, pgs.

* cited by examiner

APPLICATION INTERFACE AND DISPLAY CONTROL IN AN ANALYTE MONITORING ENVIRONMENT

CROSS-REFERENCE TO RELATED APPLICATIONS

This application claims priority to U.S. Provisional Application Ser. No. 61/921,375, filed Dec. 27, 2013, which is incorporated by reference herein in its entirety for all purposes.

FIELD

The subject matter described herein relates generally to the use of applications in an analyte monitoring environment, more particularly to control of the interfacing between applications running on the same or separate devices.

BACKGROUND

The detection and/or monitoring of analyte levels, such as glucose, ketones, lactate, oxygen, hemoglobin A1C, or the like, can be vitally important to the health of an individual having diabetes. Diabetics generally monitor their glucose levels to ensure that they are being maintained within a clinically safe range, and may also use this information to determine if and/or when insulin is needed to reduce glucose levels in their bodies or when additional glucose is needed to raise the level of glucose in their bodies.

Growing clinical data demonstrates a strong correlation between the frequency of glucose monitoring and glycemic control. Despite such correlation, many individuals diagnosed with a diabetic condition do not monitor their glucose levels as frequently as they should due to a combination of factors including convenience, testing discretion, pain associated with glucose testing, and cost. For these and other reasons, needs exist for improved analyte monitoring systems, devices, and methods.

SUMMARY

A number of systems have been developed for the automatic monitoring of the analyte(s), like glucose, in bodily fluid such as in the blood stream, in interstitial fluid ("ISF"), dermal fluid, or in other biological fluid. Some of these systems are configured so that at least a portion of a sensor control device is positioned below a skin surface of a user, e.g., in a blood vessel or in the subcutaneous tissue of a user, so that the monitoring is accomplished in vivo. As such, these systems can be referred to as "in vivo" monitoring systems. In vivo analyte monitoring systems include "Continuous Analyte Monitoring" systems (or "Continuous Glucose Monitoring" systems) that can broadcast data from a sensor control device to a reader device continuously without prompting, e.g., automatically according to a broadcast schedule. In vivo analyte monitoring systems also include "Flash Analyte Monitoring" systems (or "Flash Glucose Monitoring" systems or simply "Flash" systems) that can transfer data from a sensor control device in response to a scan or request for data by a reader device, such as with a Near Field Communication (NFC) or Radio Frequency Identification (RFID) protocol. In vivo analyte monitoring systems can also operate without the need for finger stick calibration.

The in vivo analyte monitoring systems can be differentiated from "in vitro" systems that contact a biological sample outside of the body (or rather "ex vivo") and that typically include a meter device that has a port for receiving an analyte test strip carrying bodily fluid of the user, which can be analyzed to determine the user's blood sugar level.

In vivo monitoring systems can include a sensor that, while positioned in vivo, makes contact with the bodily fluid of the user and senses the analyte levels contained therein. The sensor can be part of the sensor control device that resides on the body of the user and contains the electronics and power supply that enable and control the analyte sensing. The sensor control device, and variations thereof, can also be referred to as a "sensor control unit," an "on-body electronics" device or unit, an "on-body" device or unit, or a "sensor data communication" device or unit, to name a few.

In vivo monitoring systems can also include a device that receives sensed analyte data from the sensor control device and processes and/or displays that sensed analyte data, in any number of forms, to the user. This device, and variations thereof, can be referred to as a "reader device" (or simply a "reader"), "handheld electronics" (or a handheld), a "portable data processing" device or unit, a "data receiver," a "receiver" device or unit (or simply a receiver), or a "remote" device or unit, to name a few. Other devices such as personal computers have also been utilized with or incorporated into in vivo and in vitro monitoring systems.

Provided herein are a number of example embodiments of systems, devices, and methods that control the interfacing between applications running on a mobile device, such as a smart phone, as well as for control of the display of analyte levels and critical events. It should be noted that these embodiments are for example only and are not intended to further limit the scope of the subject matter claimed herein beyond the explicit language of the claims themselves.

Also provided are example embodiments of methods of authenticating a user interface application for operation with a sensor interface application, where these methods include receiving a request, from a user interface application, to operate with a sensor interface application, where the sensor interface application is executed by one or more processors of a device (e.g., a reader device or sensor control device), the sensor interface application being programmed to process data received from an in vivo analyte sensor, determining whether the user interface application is approved for operation with the sensor interface application, and communicating data indicative of a sensed analyte level to the user interface application if the user interface application is determined to be approved for operation with the sensor interface application. The user interface application can be responsible for outputting the sensed analyte level for display on a display of the same or a different device, depending where the user interface application resides.

In some embodiments, for example where the device is a mobile communication device, the methods can also include, after receiving the request from the user interface application, requesting information about the user interface application from an operating system of the mobile communication device, and receiving the information about the user interface application from the operating system. The information can include a name and a size of the user interface application, and an error-detecting code. In some embodiments the user interface application has a first code (or key) and the sensor interface application has a second code (or key), and the request from the user interface is encrypted with the first code.

In certain embodiments, determining whether the user interface application is approved for operation with the sensor interface application can include sending information about the user interface application to a remote registration server, and receiving an indication from the remote registration server whether the user interface application is approved for operation with the sensor interface application. These embodiments can also include, after receiving the indication from the remote registration server, assigning a registration identifier for the user interface application if the indication indicates that the user interface application is approved for operation with the sensor interface application, and communicating the registration identifier to the user interface application. The registration identifier can be a random or pseudorandom string of characters and can be assigned to a specific version of the user interface application or can be unique to that specific instance of the user interface application that is in operation with that specific instance of the sensor interface application (i.e., the identifier is not shared or reused).

In some embodiments, determining whether the user interface application is approved for operation with the sensor interface application can include determining whether the user interface application is indicated as being approved within a registration database stored on a memory of the, e.g., mobile communication device. These embodiments can include, after determining whether the user interface application is indicated as being approved within the registration database, assigning a registration identifier for the user interface application if the user interface application is indicated as being approved within the registration database, and communicating the registration identifier to the user interface application.

In some embodiments, the method further includes restricting access by the user interface application to data indicative of a sensed analyte level. The user interface application may have access to historical data indicative of a past sensed analyte level but is restricted from accessing real-time data indicative of a current sensed analyte level.

The request from the user interface application can include a time of transmission, and the methods can further include determining if the request from the user interface has expired prior to communicating data indicative of a sensed analyte level to the user interface application.

Also provided herein are example embodiments of methods of monitoring an analyte level of a human with an in vivo analyte sensor and a mobile communication device, the methods including receiving data, e.g., at the mobile communication device, from the in vivo analyte sensor, processing the received data with a sensor interface application operating on the mobile communication device to generate data representative of an analyte level of the human, communicating the data indicative of the analyte level of the human to a user interface application operating on the mobile communication device, and causing, by the user interface application, display of the analyte level of the human on a display of the mobile communication device.

These embodiments can also include granting, to the user interface application, access to the data indicative of the analyte level of the human, by the sensor interface application, prior to communicating the data indicative of the analyte level of the human to the user interface application, receiving an indication, at the sensor interface application, that access of the user interface application to the data indicative of the analyte level of the human should be removed, and removing access of the user interface application to the data indicative of the analyte level of the human.

The user interface application can be a first application adapted for the monitoring of diabetes, and the sensor interface application can also communicate with a second application adapted for the monitoring of diabetes. Certain embodiments can include the following steps performed by the sensor interface application: causing the capture of data from either the first application or the second application; and providing the captured data to the other of the first or second applications.

The methods can also include the following steps performed by the sensor interface application: determining that a critical event has occurred; and providing an indication to the user interface application that the critical event has occurred. If a confirmation was not received from the user interface application that a notification of the critical event was provided to a user, then the methods can include requesting that the user interface application provide the notification to the user. After requesting that the user interface application provide the notification, if a confirmation was not received from the user interface application that the notification was provided, then the methods can include disconnecting the user interface application from the sensor interface application, logging the critical event and sending an error message to a trusted computer system over the internet, or providing the indication to the user interface application that the critical event has occurred a second time.

If, after providing the indication to the user interface application a second time, a confirmation was not received from the user interface application that the notification was provided, then the methods can include disconnecting the user interface application from the sensor interface application, or logging the critical event and sending an error message to a trusted computer system over the internet.

In some embodiments, a confirmation of receipt of the indication that the critical event has occurred sent by the user interface application to the sensor interface application is interpreted by the sensor interface application as confirmation that the notification of the critical event was provided to a user.

The critical event can be based on an analyte level sensed in the human, such as a hypoglycemic or hyperglycemic event, or can be an error that has occurred in the in vivo analyte sensor or the sensor interface application.

Also provided herein are example embodiments of methods of monitoring an analyte level of a human with an in vivo analyte sensor and a mobile communication device, the methods including receiving measurement data, at the mobile communication device, from the in vivo analyte sensor, processing the received data with a sensor interface application operating on the mobile communication device to generate data representative of an analyte level of the human, and displaying the analyte level of the human on a display of the mobile communication device if a data age window, measured from the receipt of the measurement data from the in vivo analyte sensor, has not expired.

In some embodiments, the methods include starting a timer upon the receipt of the measurement data and verifying, prior to display of the data representative of the analyte level of the human, that the current time of the timer does not exceed the data age window. In other embodiments, the methods include recording a time at which the measurement data was received and verifying, prior to display of the data representative of the analyte level of the human, that the current time does not exceed the data age window. If the data age window has expired, the analyte level of the human can be displayed with an indication that the analyte level of the human is outside the data age window.

In certain embodiments, the methods can include, while the analyte level is displayed, monitoring a duration of time since receipt of the measurement data such that, upon expiration of the data age window, an indication that the analyte level of the human is outside the data age window is displayed. In other embodiments, the methods can include, while the analyte level is displayed, monitoring a duration of time since receipt of the measurement data such that, upon expiration of the data age window, the analyte level of the human is no longer displayed.

Displaying the analyte level of the human on a display of the mobile communication device can, in some embodiments, include displaying the analyte level of the human on the display for a predetermined minimum duration. The predetermined minimum duration can be determined such that it does not include any time during which the analyte level of the human is not displayed as a result of an application that is responsible for causing the display of the analyte level of the human having been inactivated. The application that is responsible for causing the display of the analyte level of the human can be the sensor interface application or the user interface application. Inactivation can be caused by a user actuating a home button of the mobile communication device.

In certain embodiments, the methods can include displaying an alarm or warning related to a critical event and, if the alarm or warning is not displayed for a predetermined minimum duration, then providing a secondary alarm or warning to the user. The secondary alarm or warning can be in the form of a text message, vibration, or auditory signal. If the secondary alarm or warning is a first secondary alarm or warning, the methods can further include, if no confirmation is obtained that the user has received the first secondary alarm or warning, then providing a second secondary alarm or warning to the user. In some embodiments, the first secondary alarm includes a visual indication, and the second secondary alarm includes a visual indication and a tactile or auditory indication.

For each and every embodiment of a method disclosed herein, systems and devices capable of performing each of those embodiments are covered within the scope of the present disclosure. For example, embodiments of reader devices are disclosed having one or more transmitters, receivers, memories, power sources, processors and/or controllers. These embodiments of the reader devices can be used to implement those steps that can logically be performed by a reader device from any and all of the methods described herein.

Likewise, embodiments of trusted computer systems are also disclosed. These trusted computer systems can include one or more processors, controllers, transmitters, receivers, memories, databases, servers, and/or networks, and can be discretely located or distributed across multiple geographic locales. These embodiments of the trusted computer systems can be used to implement those steps that can logically be performed by a trusted computer system from any and all of the methods described herein.

Embodiments of sensor control devices are also disclosed and these devices can have one or more sensors, analyte monitoring circuits (e.g., an analog circuit), memories, power sources, communication circuits (e.g., transmitters, receivers, transceivers), processors, and/or controllers. These sensor control device embodiments can be used and can be capable of use to implement those steps that can logically be performed by a sensor control device from any and all of the methods described herein.

Referring back to the reader devices, many are provided herein that can include software instructions, executable on one or more processors of the reader device, for executing many of the described method steps. The reader devices are generally devices that include an operating system and one or more applications running thereon.

For example, embodiments of mobile communication devices are provided, wherein the devices include a non-transitory memory on which a sensor interface application is stored, an RF transceiver adapted to receive data from an in vivo analyte sensor, and at least one processor communicatively coupled with the non-transitory memory and the RF transceiver, the at least one processor being adapted to execute the sensor interface application and adapted to: receive a request, from a user interface application, to operate with the sensor interface application, the sensor interface application being programmed to process data received from the in vivo analyte sensor; determine whether the user interface application is approved for operation with the sensor interface application; and communicate data indicative of a sensed analyte level to the user interface application if the user interface application is determined to be approved for operation with the sensor interface application.

In some embodiments, the at least one processor is adapted to: after receiving the request from the user interface application, request information about the user interface application from an operating system of the mobile communication device; and receive the information about the user interface application from the operating system. The user interface application can be associated with a first code and the sensor interface application can be associated with a second code, and the request from the user interface can be encrypted with the first code. The at least one processor can be adapted to decrypt the request with the second code.

In certain embodiments, the at least one processor can be adapted to: cause information about the user interface application to be sent to a remote registration server; and process an indication from the remote registration server whether the user interface application is approved for operation with the sensor interface application.

The at least one processor can be adapted to: after receiving the indication from the remote registration server, assign a registration identifier for the user interface application if the indication indicates that the user interface application is approved for operation with the sensor interface application; and communicate the registration identifier to the user interface application.

In some embodiments, the at least one processor is adapted to determine whether the user interface application is indicated as being approved within a registration database stored on a memory of the mobile communication device. The at least one processor can be adapted to, after determining whether the user interface application is indicated as being approved within the registration database, assign a registration identifier for the user interface application if the user interface application is indicated as being approved within the registration database, and communicate the registration identifier to the user interface application. The at least one processor can be adapted to restrict access by the user interface application to data indicative of a sensed analyte level. In some embodiments, the user interface application has access to historical data indicative of a past sensed analyte level but is restricted from accessing real-time data indicative of a current sensed analyte level.

The at least one processor can be adapted to execute the user interface application and output the sensed analyte level for display on a display of the mobile communication device.

Also provided are example embodiments of mobile communication devices that include a non-transitory memory on which a sensor interface application is stored, an RF transceiver adapted to receive data from an in vivo analyte sensor, and at least one processor communicatively coupled with the non-transitory memory and the RF transceiver and adapted to execute the sensor interface application, process the received data with a sensor interface application to generate data representative of an analyte level of the human, communicate the data indicative of the analyte level of the human to a user interface application, and cause display of the analyte level of the human on a display of the mobile communication device.

In some embodiments, the at least one processor is adapted to grant, to the user interface application, access to the data indicative of the analyte level of the human, by the sensor interface application, prior to communicating the data indicative of the analyte level of the human to the user interface application, receive an indication, at the sensor interface application, that access of the user interface application to the data indicative of the analyte level of the human should be removed, and remove access of the user interface application to the data indicative of the analyte level of the human.

The user interface application can be a first application adapted for the monitoring of diabetes, and the sensor interface application can also communicate with a second application adapted for the monitoring of diabetes. The at least one processor can be adapted to cause the capture of data from either the first application or the second application and provide the captured data to the other of the first or second applications.

In certain embodiments, the at least one processor is adapted to determine that a critical event has occurred and provide an indication to the user interface application that the critical event has occurred, and if a confirmation was not received from the user interface application that a notification of the critical event was provided to a user, then request that the user interface application provide the notification to the user. At least one processor can be adapted to, after a request that the user interface application provide the notification, if a confirmation is not received from the user interface application that the notification was provided, then disconnect the user interface application from the sensor interface application, log the critical event and cause an error message to be sent to a trusted computer system over the internet, or provide the indication to the user interface application that the critical event has occurred a second time. If, after the indication is provided to the user interface application a second time, a confirmation is not received from the user interface application that the notification was provided, then the at least one processor can disconnect the user interface application from the sensor interface application or log the critical event and cause an error message to be sent to a trusted computer system over the internet.

Other embodiments of mobile communication devices are also provided that include a display, a non-transitory memory on which a sensor interface application is stored, an RF transceiver adapted to receive data from an in vivo analyte sensor, and at least one processor communicatively coupled with the display, the non-transitory memory, and the RF transceiver, wherein the at least one processor is adapted to execute the sensor interface application and adapted to: process the received data with the sensor interface application to generate data representative of an analyte level of the human; and display the analyte level of the human on the display of the mobile communication device if a data age window, measured from the receipt of the measurement data from the in vivo analyte sensor, has not expired.

In some embodiments, the at least one processor is adapted to start a timer upon the receipt of the measurement data and verify, prior to display of the data representative of the analyte level of the human, that the current time of the timer does not exceed the data age window. In other embodiments, the at least one processor can be adapted to record a time at which the measurement data was received and verify, prior to display of the data representative of the analyte level of the human, that the current time does not exceed the data age window. If the data age window has expired, the at least one processor can cause the display of the analyte level of the human with an indication that the analyte level of the human is outside the data age window.

The at least one processor can also be adapted to monitor, while the analyte level is displayed, a duration of time since receipt of the measurement data such that, upon expiration of the data age window, either an indication that the analyte level of the human is outside the data age window is displayed or the analyte level of the human is no longer displayed.

In some embodiments, the at least one processor is adapted to cause the analyte level of the human to be displayed on the display for a predetermined minimum duration. The predetermined minimum duration may not include any time during which the analyte level of the human is not displayed as a result of an application that is responsible for causing the display of the analyte level of the human having been inactivated.

The at least one processor can also be adapted to cause an alarm or warning related to a critical event to be displayed and, if the alarm or warning is not displayed for a predetermined minimum duration, then provide a secondary alarm or warning to the user. The secondary alarm or warning can be a first secondary alarm or warning, and the at least one processor can be adapted to, if no confirmation is obtained that the user has received the first secondary alarm or warning, provide a second secondary alarm or warning to the user. In some embodiments, the first secondary alarm includes a visual indication and the second secondary alarm includes a visual indication and a tactile or auditory indication.

Other systems, devices, methods, features and advantages of the subject matter described herein will be or will become apparent to one with skill in the art upon examination of the following figures and detailed description. It is intended that all such additional systems, devices, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF THE FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

DETAILED DESCRIPTION

Figure 1:
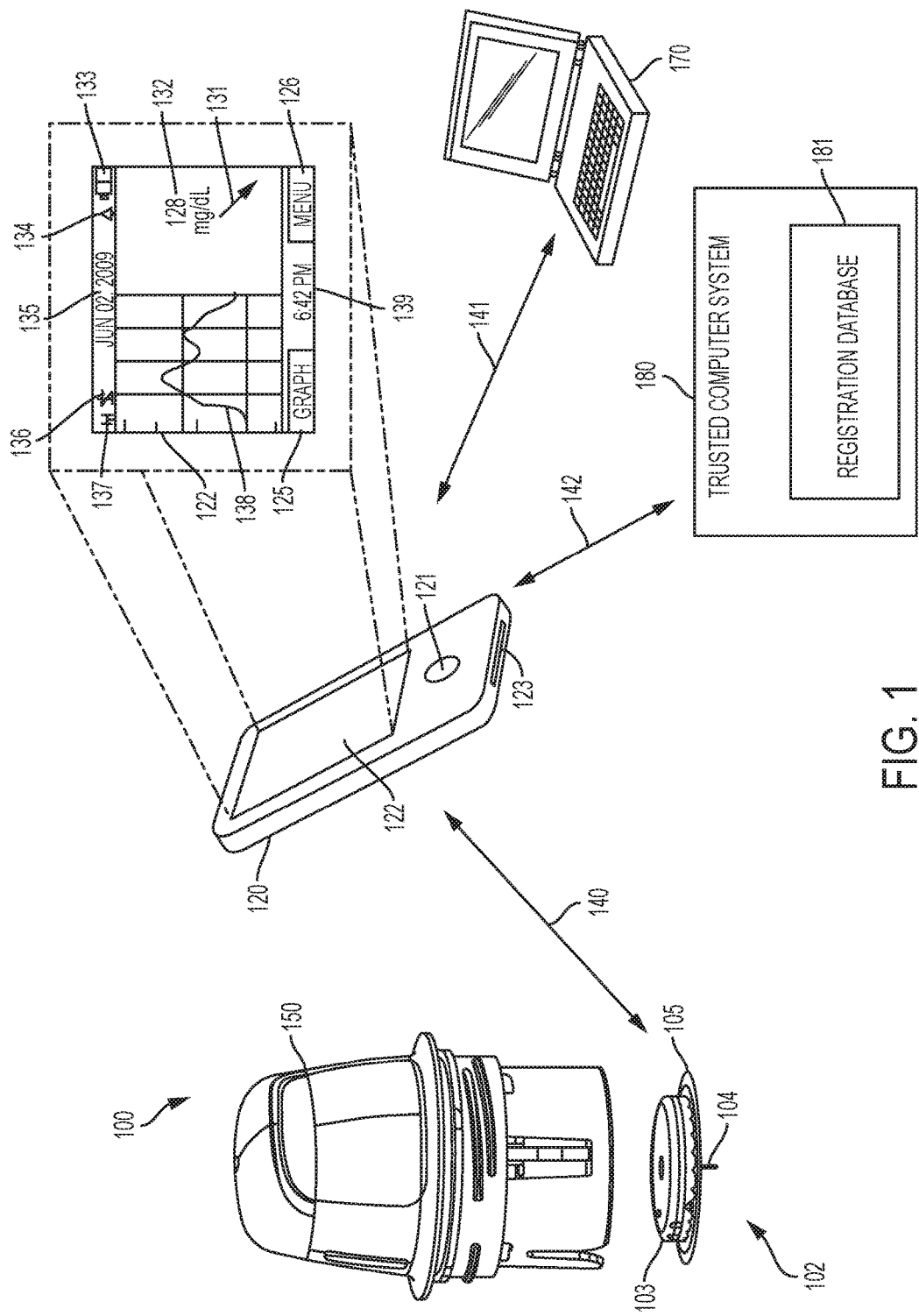
FIG. 1 is a high level diagram depicting an example embodiment of an analyte monitoring system for real time analyte (e.g., glucose) measurement, data acquisition and/or processing.

Before the present subject matter is described in detail, it is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

As used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

Generally, embodiments of the present disclosure are used with in vivo systems, devices, and methods for detecting at least one analyte, such as glucose, in body fluid (e.g., transcutaneously, subcutaneously within the ISF or blood, or within the dermal fluid of the dermal layer). Accordingly, many embodiments include in vivo analyte sensors arranged so that at least a portion of the sensor is positioned in the body of a user to obtain information about at least one analyte of the body. It should be noted, however, that the embodiments disclosed herein can be used with in vivo analyte monitoring systems that incorporate in vitro capability, as well has purely in vitro or ex vivo analyte monitoring systems.

The embodiments described herein relate generally to the manner of authentication and/or interaction between a sensor interface application running on a first device, e.g., a smart phone, and another application, such as a user interface application, running on the same or a different device.

Proper interaction between these applications is important to the proper operation of in vivo analyte monitoring systems, and this interaction can be made more challenging when the applications are designed and written by different parties. For example, the sensor interface application, which can be responsible for processing data received from a sensor control device, may in some embodiments be provided by the manufacturer of the sensor control device, while the user interface application, which can be responsible for display of sensed analyte data to the user, may in some embodiments be provided by a third party.

Certain embodiments described herein relate to the display of sensed analyte data to the user in a timely and controlled fashion, either directly by the sensor interface application (e.g., having user interface capability) or by a separate user interface application.

Before describing these application interface aspects and analyte display aspects of the embodiments in detail, however, it is first desirable to describe examples of devices that can be present within an in vivo analyte monitoring system as well as examples of their operation. FIG. 1 is an illustrative view depicting an example of an in vivo analyte monitoring system 100 having a sensor control device 102 and a reader device 120 that communicate with each other over a local communication path (or link) 140, which can be wired or wireless, and uni-directional or bi-directional. In embodiments where path 140 is wireless, a near field communication (NFC) protocol, RFID protocol, Bluetooth or Bluetooth Low Energy protocol, Wi-Fi protocol, proprietary protocol, or the like can be used.

Reader device 120 is also capable of wired, wireless, or combined communication with a remote computer system 170 over communication path (or link) 141 and with trusted computer system 180 over communication path (or link) 142. Communication paths 141 and 142 can be part of a telecommunications network, such as a Wi-Fi network, a local area network (LAN), a wide area network (WAN), the internet, or other data network for uni-directional or bi-directional communication. In an alternative embodiment, communication paths 141 and 142 can be the same path. All communications over paths 140, 141, and 142 can be encrypted and sensor control device 102, reader device 120, remote computer system 170, and trusted computer system 180 can each be configured to encrypt and decrypt those communications sent and received.

Sensor control device 102 can include a housing 103 containing in vivo analyte monitoring circuitry and a power source (see, e.g., device 102 as described in the '225 Publication incorporated below). The in vivo analyte monitoring circuitry is electrically coupled with an analyte sensor 104 that extends through an adhesive patch 105 and projects away from housing 103. Adhesive patch 105 contains an adhesive layer (not shown) for attachment to a skin surface of the body of the user. (Other forms of body attachment to the body may be used, in addition to or instead of adhesive.)

Sensor 104 is adapted to be at least partially inserted into the body of the user, where it can make fluid contact with that user's body fluid (e.g., interstitial fluid (ISF), dermal fluid, or blood) and be used, along with the in vivo analyte monitoring circuitry, to measure analyte-related data of the user. Sensor 104 and any accompanying sensor control electronics can be applied to the body in any desired manner. For example, also shown in FIG. 1 is an embodiment of insertion device 150 that, when operated, transcutaneously (or subcutaneously) positions a portion of analyte sensor 104 through the user's skin and into contact with the bodily fluid, and positions sensor control device 102 with adhesive patch 105 onto the skin. In other embodiments, insertion device 150 can position sensor 104 first, and then accompanying sensor control electronics can be coupled with sensor 104 afterwards, either manually or with the aid of a mechanical device. Other devices, systems, and methods that may be used with embodiments herein, including variations of sensor control device 102, are described, e.g., in U.S. Publications 2010/0324392, 2011/0106126, 2011/0190603, 2011/0191044, 2011/0082484, 2011/0319729, and 2012/0197222, the disclosures of each of which are incorporated herein by reference for all purposes.

After collecting the analyte-related data, sensor control device 102 can then wirelessly communicate that data (such as, for example, data corresponding to monitored analyte level and/or monitored temperature data, and/or stored historical analyte related data) to a reader device 120 where, in certain embodiments, it can be algorithmically processed into data representative of the analyte level of the user and then displayed to the user and/or otherwise incorporated into a diabetes monitoring regime.

As shown in FIG. 1, reader device 120 includes a display 122 to output information to the user and/or to accept an input from the user (e.g., if configured as a touch screen), and one optional input component 121 (or more), such as a button, actuator, touch sensitive switch, capacitive switch, pressure sensitive switch, jog wheel or the like, to input data or commands to reader device 120 or otherwise control the operation of reader device 120.

In certain embodiments, input component 121 of reader device 120 may include a microphone and reader device 120 may include software configured to analyze audio input received from the microphone, such that functions and operation of the reader device 120 may be controlled by voice commands. In certain embodiments, an output component of reader device 120 includes a speaker (not shown) for outputting information as audible signals. Similar voice responsive components such as a speaker, microphone and software routines to generate, process and store voice driven signals may be provided to sensor control device 102.

In certain embodiments, display 122 and input component 121 may be integrated into a single component, for example a display that can detect the presence and location of a physical contact touch upon the display such as a touch screen user interface. In such embodiments, the user may control the operation of reader device 120 by utilizing a set of pre-programmed motion commands, including, but not limited to, single or double tapping the display, dragging a finger or instrument across the display, motioning multiple fingers or instruments toward one another, motioning multiple fingers or instruments away from one another, etc. In certain embodiments, a display includes a touch screen having areas of pixels with single or dual function capacitive elements that serve as LCD elements and touch sensors.

Reader device 120 also includes one or more data communication ports 123 for wired data communication with external devices such as a remote terminal, e.g., a personal computer. Example data communication ports include USB ports, mini USB ports, RS-232 ports, Ethernet ports, Firewire ports, or other similar data communication ports configured to connect to the compatible data cables. Reader device 120 may also include an integrated or attachable in vitro glucose meter, including an in vitro test strip port (not shown) to receive an in vitro glucose test strip for performing in vitro blood glucose measurements.

Referring still to FIG. 1, display 122 can be configured to display a variety of information—some or all of which may be displayed at the same or different time on display 122. The displayed information can be user-selectable so that a user can customize the information shown on a given display screen. Display 122 may include, but is not limited to, graphical display 138, for example, providing a graphical output of glucose values over a monitored time period (which may show: markers such as meals, exercise, sleep, heart rate, blood pressure, etc.; numerical display 132, for example, providing monitored glucose values (acquired or received in response to the request for the information); and trend or directional arrow display 131 that indicates a rate of analyte change and/or a rate of the rate of analyte change, e.g., by moving locations on display 122).

As further shown in FIG. 1, display 122 may also include: date display 135, which can provide date information for the user; time of day information display 139 providing time of day information to the user; battery level indicator display 133 graphically showing the condition of the battery (rechargeable or disposable) of reader device 120; sensor calibration status icon display 134, for example, in monitoring systems that require periodic, routine or a predetermined number of user calibration events notifying the user that the analyte sensor calibration is necessary; audio/vibratory settings icon display 136 for displaying the status of the audio/vibratory output or alarm state; and wireless connectivity status icon display 137 that provides indication of wireless communication connection with other devices such as sensor control device 102, remote computer system 170, and/or trusted computer system 180. Display 122 may further include simulated touch screen buttons 125, 126 for accessing menus, changing display graph output configurations or otherwise for controlling the operation of reader device 120.

In certain embodiments, reader device 120 can be configured to output alarms, alert notifications, glucose values, etc., which may be visual, audible, tactile, or any combination thereof. Reader device 120 may include other output components such as a speaker, vibratory output component and the like to provide audible and/or vibratory output indications to the user in addition to the visual output indication provided on display 122. Further details and other display embodiments can be found in, e.g., U.S. Publication 2011/0193704, which is incorporated herein by reference for all purposes.

Reader device 120 can be connected to a remote terminal 170, such as a personal computer, which can be used by the user or a medical professional to display and/or analyze the collected analyte data. Reader device 120 can also be connected to a trusted computer system 180 that can be used for authentication of a third party software application. In both instances, reader device 120 can function as a data conduit to transfer the stored analyte level information from the sensor control device 102 to remote terminal 170 or trusted computer system 180. In certain embodiments, the received data from the sensor control device 102 may be stored (permanently or temporarily) in one or more memories of reader device 120.

Remote terminal 170 may be a personal computer, a server terminal, a laptop computer, a tablet, or other suitable data processing device. Remote terminal 170 can be (or include) software for data management and analysis and communication with the components in analyte monitoring system 100. Operation and use of remote terminal 170 is further described in the incorporated '225 Publication. Analyte monitoring system 100 can also be configured to operate with a data processing module (not shown), also as described in the incorporated '225 Publication.

Trusted computer system 180 can also be referred to as registration computer system 180, or simply computer system 180. Trusted computer system 180 can include one or more computers, servers, networks, databases, and the like.

Trusted computer system 180 can be within the possession of the manufacturer or distributor of sensor control device 102, either physically or virtually through a secured connection, and can be used to perform authentication of third-party software applications. Authentication of third-party software applications can also be outsourced to a trusted third-party, such that the trusted third-party is physically in possession of trusted computer system 180. Trusted computer system 180 is trusted in the sense that system 100 can assume that it provides valid information and determinations upon which a foundation for the authentication activities can be based. Trusted computer system 180 can be trusted simply by virtue of it being within the possession or control of the manufacturer, e.g., like a typical web server. Alternatively, trusted computer system 180 can be implemented in a more secure fashion such as by requiring additional password, encryption, firewall, or other internet access security enhancements that further guard against counterfeiter attacks or attacks by computer hackers.

The processing of data within system 100 can be performed by one or more control logic units or processors of reader device 120, remote terminal 170, trusted computer system 180, and/or sensor control device 102. For example, raw data measured by sensor 104 can be algorithmically processed into a value that represents the analyte level and that is readily suitable for display to the user, and this can occur in sensor control device 102, reader device 120, remote terminal 170, or trusted computer system 180. This and any other information derived from the raw data can be displayed in any of the manners described above (with respect to display 122) on any display residing on any of sensor control device 102, reader device 120, remote terminal 170, or trusted computer system 180.

The information may be utilized by the user to determine any necessary corrective actions to ensure the analyte level remains within an acceptable and/or clinically safe range. Other visual indicators, including colors, flashing, fading, etc., as well as audio indicators, including a change in pitch, volume, or tone of an audio output, and/or vibratory or other tactile indicators may also be incorporated into the outputting of trend data as means of notifying the user of the current level, direction, and/or rate of change of the monitored analyte level. For example, based on a determined rate of glucose change, programmed clinically significant glucose threshold levels (e.g., hyperglycemic and/or hypoglycemic levels), and current analyte level derived by an in vivo analyte sensor, an algorithm stored on a computer readable medium of system 100 can be used to determine the time it will take to reach a clinically significant level and can be used to output a notification in advance of reaching the clinically significant level, e.g., 30 minutes before a clinically significant level is anticipated, and/or 20 minutes, and/or 10 minutes, and/or 5 minutes, and/or 3 minutes, and/or 1 minute, and so on, with outputs increasing in intensity or the like.

Referring now in further detail to reader device 120, that device 120 can be a mobile communication device such as a mobile telephone including, but not limited to, a Wi-Fi or internet enabled smart phone, tablet, or personal digital assistant (PDA). Examples of smart phones can include those mobile phones based on a Windows® operating system, Android™ operating system, iPhone® operating system, Palm® WebOS™, Blackberry® operating system, or Symbian® operating system, with data network connectivity functionality for data communication over an internet connection and/or a local area network (LAN).

Reader device 120 can also be configured as a mobile smart wearable electronics assembly, such as an optical assembly that is worn over or adjacent to the user's eye (e.g., a smart glass or smart glasses, such as Google glasses, which is a mobile communication device). This optical assembly can have a transparent display that displays information about the user's analyte level (as described herein) to the user while at the same time allowing the user to see through the display such that the user's overall vision is minimally obstructed. The optical assembly may be capable of wireless communications similar to a smart phone. Other examples of wearable electronics include devices that are worn around or in the proximity of the user's wrist (e.g., a watch, etc.), neck (e.g., a necklace, etc.), head (e.g., a headband, hat, etc.), chest, or the like.

Figure 2A:
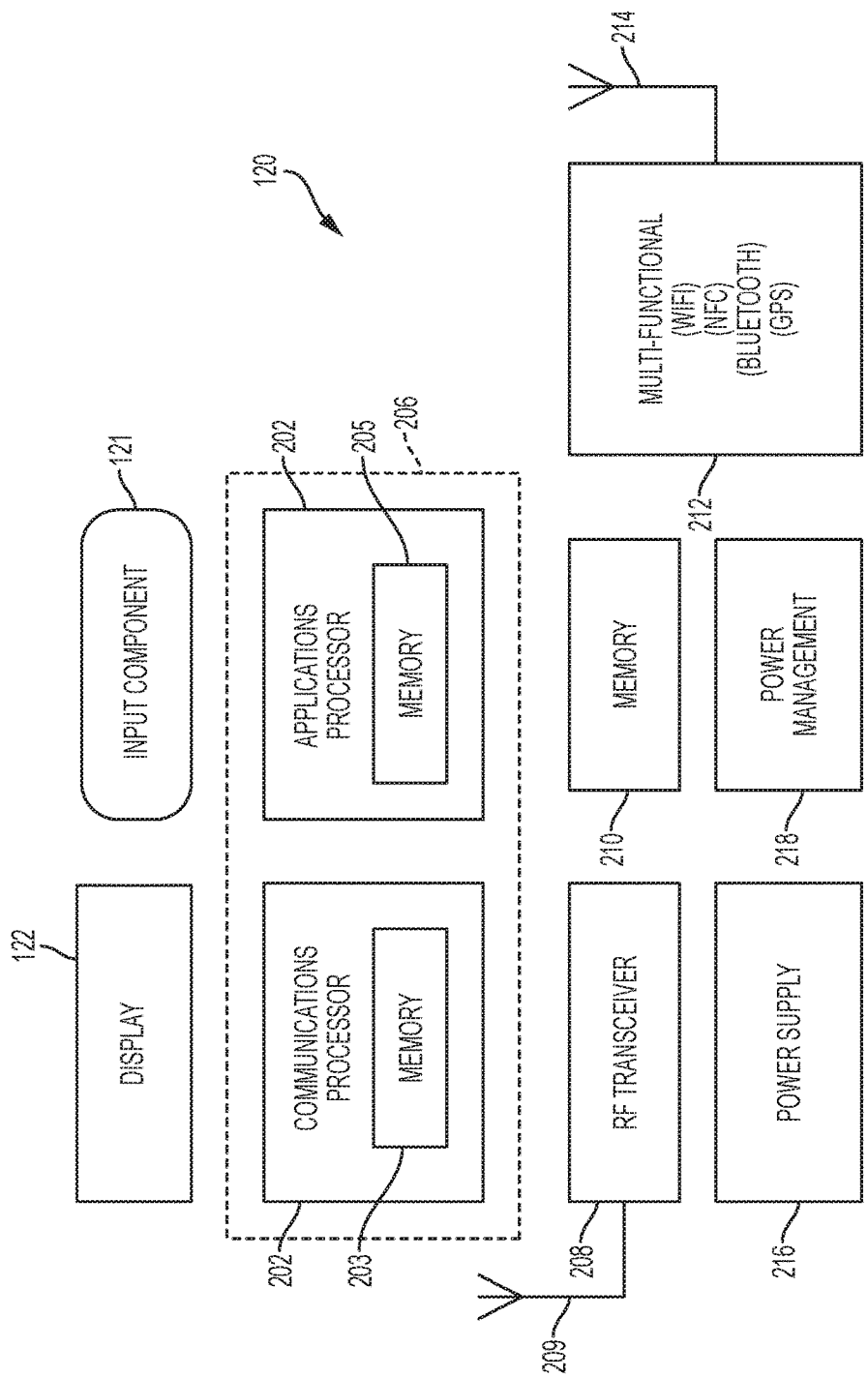
FIG. 2A is a block diagram depicting an example embodiment of a reader device configured as a smart phone.

FIG. 2A is a block diagram of an example embodiment of a reader device 120 configured as a smart phone. Here, reader device 120 includes an input component 121, display 122, and processing hardware 206, which can include one or more processors, microprocessors, controllers, and/or microcontrollers, each of which can be a discrete chip or distributed amongst (and a portion of) a number of different chips. Here, processing hardware 206 includes a communications processor 202 having on-board memory 203 and an applications processor 204 having on-board memory 205. Reader device 120 further includes an RF transceiver 208 coupled with an RF antenna 209, a memory 210, multi-functional circuitry 212 with one or more associated antennas 214, a power supply 216, and power management circuitry 218. FIG. 2A is an abbreviated representation of the typical hardware and functionality that resides within a smart phone, but other hardware and functionality (e.g., codecs, drivers, glue logic, etc.) can also be included here.

Communications processor 202 can interface with RF transceiver 208 and perform analog-to-digital conversions, encoding and decoding, digital signal processing and other functions that facilitate the conversion of voice, video, and data signals into a format (e.g., in-phase and quadrature) suitable for provision to RF transceiver 208, which can then transmit the signals wirelessly. Communications processor 202 can also interface with RF transceiver 208 to perform the reverse functions necessary to receive a wireless transmission and convert it into digital data, voice, and video.

Figure 2B:
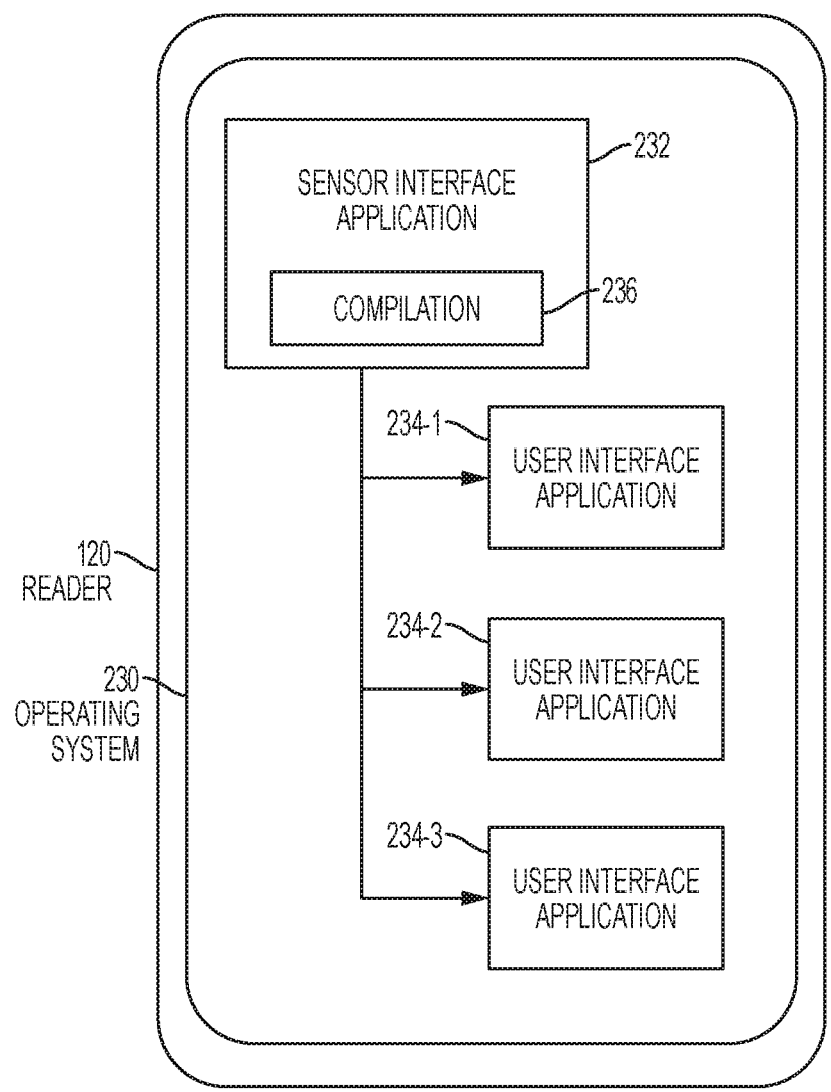
FIG. 2B is a block diagram depicting several applications related to a diabetes monitoring regime being executed by a reader device.

Applications processor 204 can be adapted to execute the operating system and any software applications that reside on reader device 120, process video and graphics, and perform those other functions not related to the processing of communications transmitted and received over RF antenna 209. FIG. 2B is a block diagram depicting an example embodiment of the software being executed on the smart phone reader device 120. The smart phone operating system 230 operates in conjunction with a number of applications on reader device 120. Any number of applications can be running on reader device 120 at any one time, and will typically include one or more applications that are related to a diabetes monitoring regime, in addition to the other commonly used applications that are unrelated to such a regime, e.g., email, calendar, weather, sports, games, etc.

FIG. 2B depicts several applications related to a diabetes monitoring regime that are running on reader device 120, including an instance of a sensor interface application 232 and three instances of user interface applications 234-1, 234-2, and 234-3. The sensor interface application 232 can be programmed to initiate communications with sensor control device 102 (e.g., a request for an analyte measurement to be performed, a request for already measured data to be communicated to reader device 120, and others) and process data received from sensor control device 102 (e.g., convert raw data received from sensor control device 102 into a value representative of the current or historical analyte level of the wearer (who is typically also the user)). In other embodiments, sensor interface application 232 can be executed on sensor control device 102, remote terminal 170, or trusted computer system 180.

In some embodiments, sensor interface application 232 and user interface application 234 can both be executed by one or more processors of the same device, such as reader device 120 as described with respect to FIG. 2B. Alternatively, the processing and display functionality of reader device 120 can be integrated into sensor control device 102, such that a separate reader device 120 is not necessary. Such an integrated sensor control device 102 could resemble a smart watch or other wearable smart electronics. In other embodiments, sensor interface application 232 and user interface application 234 are each executed on different devices, such as sensor control device 102 (for sensor interface application 232) and reader device 120 (for user interface application 234), and communicate over communication path 140 (FIG. 1).

User interface applications 234 are each programmed to interact with sensor interface application 232 and the user of reader device 120 (which can be the wearer of sensor control device 102, a medical professional, or another). In many embodiments, at least one of the user interface applications 234 acts as a tool for displaying current or historical analyte data of the user. That user interface application 234 can be programmed to accept current or historical analyte data from sensor interface application 232 and display (or cause to be displayed) that analyte data to the user in any of the forms described herein (e.g., graphical display 138, numerical display 132, trend or directional arrow display 131) or others. User interface application 234 can also display any other information desired, including but not limited to date display 135, time of day information display 139, battery level indicator display 133, sensor calibration status icon display 134, audio/vibratory settings icon display 136, wireless connectivity status icon display 137, information about the status of the wireless connection (e.g., connected/disconnected, strength of signal, etc.) with sensor control device 102, and simulated touch screen buttons 125, 126.

The term "user interface application" refers broadly to applications that interface with a user, such as those provided by third parties, other than sensor interface application 232 (which may or may not directly interface with the user). (The term "third party" generally refers to a party different than the entity that provides sensor interface application 232 and sensor control device 102, that entity typically being the manufacturer.) Accordingly, the functions that can be performed by user interface application 234 are almost limitless, and can extend well beyond simple display of the analyte results to the user. User interface applications 234 can perform other tasks including the tracking of daily activities, the tracking of insulin, the counting of dietary intake (e.g., carbohydrates, calories, alcohol, sugars, starches, and/or fats, etc.), the tracking of medications ingested and their dosages, the tracking of the state of health of the user, the tracking of the user's sleep schedule, and/or the tracking of the user's fitness level or activities. In one example, third party health care groups can provide a user interface application 234 that automatically uploads the user's diabetes monitoring data to the health care group's electronic record for that user. In another example, user interface application 234 can periodically analyze the user's diabetes monitoring data and give coaching feedback.

Each user interface application 234 can make use of the analyte data in a different way and provide a different focus for managing the user's health. The functions that user interface applications 234 provide for the user may overlap with each other, and may even overlap with user interface functions of sensor interface application 232. Each user interface application 234 can be free to interact with each other and sensor interface application 232.

For example, a number of user interface applications 234 may cooperate to enable the user to count or track consumed carbohydrates. A first user interface application 234 may provide an extensive list of foods for the user to choose from, while a second user interface application 234 may allow the user to use the camera on the phone (reader device 120) to assess portion size, while a third user interface application 234 might have a feature that offers healthier substitutes for menu items.

Each of the three user interface applications 234 can display the current and historic analyte levels obtained from sensor interface application 232. Each application 234 may display the analyte level in addition to its other features, or it may base a calculation on the current analyte level, or base it on historical trends of the user's analyte levels (or values). For example, one or more of user interface applications 234 can predict a future analyte level based on the estimated carbohydrates in a meal the user is about to eat, as well as the user's current analyte level and recent history. In another example, one or more of applications 234 could incorporate recommended insulin doses to offset an estimated carbohydrate intake or an application 234 could offer a choice of controlling portions to let the user eat more of their favorite food (e.g., less bread equals more potatoes) and keep the total within their intake target.

Referring back to FIG. 2A, memory 210 can be shared by one or more the various functional units present within reader device 120, or can be distributed amongst two or more of them (e.g., as separate memories present within different chips). Memory 210 can also be a separate chip of its own. Memory 210 is non-transitory, and can be volatile (e.g., RAM, etc.) and/or non-volatile memory (e.g., ROM, flash memory, F-RAM, etc.).

Multi-functional circuitry 212 can be implemented as one or more chips and/or components that perform other functions such as local wireless communications (e.g., Wi-Fi, Bluetooth, Bluetooth Low Energy) and determining the geographic position of reader device 120 (e.g., global positioning system (GPS) hardware). One or more other antennas 214 are associated with both the functional circuitry 212 as needed.

Power supply 216 can include one or more batteries, which can be rechargeable or single-use disposable batteries. Power management circuitry 218 can regulate battery charging and power supply monitoring, boost power, perform DC conversions, and the like.

As mentioned, the reader device 120 may also include one or more data communication ports such as USB port (or connector) or RS-232 port (or any other wired communication ports) for data communication with a remote terminal 170, trusted computer system 180, or sensor control device 102, to name a few.

Reader device 120 may include a strip port (not shown) or be coupled with a strip port module (not shown) configured to receive in vitro test strips. In such a configuration, reader device 120 can process a fluid sample on a test strip, determine an analyte level contained therein, and display that result to a user. Any suitable in vitro test strip may be employed, e.g., test strips that only require a very small amount (e.g., one microliter or less, e.g., about 0.5 microliter or less, e.g., about 0.1 microliter or less), of applied sample to the strip in order to obtain accurate glucose information, e.g. FreeStyle® or Precision® blood glucose test strips and systems from Abbott Diabetes Care Inc. Reader devices with in vitro monitors and test strip ports may be configured to conduct in vitro analyte monitoring with no user calibration in vitro test strips (i.e., no human intervention calibration), such as FreeStyle Lite glucose test strips from Abbott Diabetes Care Inc. Detailed description of such test strips and devices for conducting in vitro analyte monitoring is provided in U.S. Pat. Nos. 6,377,894, 6,616,819, 7,749,740, 7,418,285; U.S. Published Patent Publication Nos. 2004/0118704, 2006/0091006, 2008/0066305, 2008/0267823, 2010/0094110, 2010/0094111, and 2010/0094112, and 2011/0184264, the disclosure of each of which are incorporated herein by reference for all purposes. The present inventive subject matter can be used with and/or in the systems, devices, and methods described in these incorporated references.

Referring back to the in vivo environment, information may be communicated from sensor control device 102 to reader device 120 automatically and/or continuously when the analyte information is available, or may not be communicated automatically and/or continuously, but rather stored or logged in a memory of sensor control device 102, e.g., for later output. Accordingly, in many embodiments of system 100, analyte information derived by sensor control device 102 is made available in a user-usable or viewable form only when queried by the user such that the timing of data communication is selected by the user.

Data can be sent from sensor control device 102 to reader device 120 at the initiative of either sensor control device 102 or reader device 120. For example, in some example embodiments sensor control device 102 can communicate data periodically in a broadcast-type fashion, such that an eligible reader device 120, if in range and in a listening state, can receive the communicated data (e.g., sensed analyte data). This is at the initiative of sensor control device 102 because reader device 120 does not have to send a request or other transmission that first prompts sensor control device 102 to communicate. Broadcasts can be performed, for example, using an active WiFi, Bluetooth, or BTLE connection. The broadcasts can occur according to a schedule that is programmed within device 102 (e.g., about every 1 minute, about every 5 minutes, about every 10 minutes, or the like). Broadcasts can also occur in a random or pseudorandom fashion, such as whenever sensor control device 102 detects a change in the sensed analyte data. Further, broadcasts can occur in a repeated fashion regardless of whether each broadcast is actually received by a reader device 120.

System 100 can also be configured such that reader device 120 sends a transmission that prompts sensor control device 102 to communicate its data to reader device 120. This is generally referred to as "on-demand" data transfer. An on-demand data transfer can be initiated based on a schedule stored in the memory of reader device 120, or at the behest of the user via a user interface of reader device 120. For example, if the user wants to check his or her analyte level, the user could perform a scan of sensor control device 102 using an NFC, Bluetooth, BTLE, or WiFi connection. Data exchange can be accomplished using broadcasts only, on-demand transfers only, or any combination thereof.

Accordingly, once a sensor control device 102 is placed on the body so that at least a portion of sensor 104 is in contact with the bodily fluid and electrically coupled to the electronics within device 102, sensor derived analyte information may be communicated in on-demand or broadcast fashion from the sensor control device 102 to a reader device 120. On-demand transfer can occur by first powering on reader device 120 (or it may be continually powered) and executing a software algorithm stored in and accessed from a memory of reader device 120 to generate one or more requests, commands, control signals, or data packets to send to sensor control device 102. The software algorithm can be part of either sensor interface application 232 or user interface application 234. The software algorithm executed under, for example, the control of processing hardware 206 of reader device 120 may include routines to detect the position of the sensor control device 102 relative to reader device 120 to initiate the transmission of the generated request command, control signal and/or data packet.

The programming stored in memory for execution by processing hardware 206 that generates and causes the transmission of the one or more requests, commands, control signals, or data packets to sensor control device 102 can be a part of sensor interface application, user interface application 234, or a combination thereof. For example, a request for data from sensor control device 102 that is part of a predetermined schedule may be generated entirely by sensor interface application 232. On the other hand, when the user affirmatively requests a current analyte measurement (e.g., in response to a user activation of input component 121, such as by depressing a button, triggering a soft button associated with the data communication function, issuing a voice command or audible signal to a microphone of reader device 120, which is processed by a voice recognition software within reader device 120, and the like), then user interface application 234 can be responsible for receiving the user's request and informing sensor interface application 232 that a request needs to be performed, at which time sensor interface application 232 can generate the request and cause it to be transmitted to sensor control device 102. In certain embodiments, positioning sensor control device 102 and reader device 120 within a predetermined distance (e.g., close proximity) relative to each other initiates one or more software routines of reader device 120 to generate and transmit a request, command, control signal, or data packet.

Different types and/or forms and/or amounts of information may be sent as part of each on-demand or broadcast transmission including, but not limited to, one or more of current analyte level information (i.e., real time or the most recently obtained analyte level information temporally corresponding to the time the reading is initiated), rate of change of an analyte over a predetermined time period, rate of the rate of change of an analyte (acceleration in the rate of change), or historical analyte information corresponding to analyte information obtained prior to a given reading and stored in a memory of sensor control device 102.

Some or all of real time, historical, rate of change, rate of rate of change (such as acceleration or deceleration) information may be sent to reader device 120 in a given communication or transmission. In certain embodiments, the type and/or form and/or amount of information sent to reader device 120 may be preprogrammed and/or unchangeable (e.g., preset at manufacturing), or may not be preprogrammed and/or unchangeable so that it may be selectable and/or changeable in the field one or more times (e.g., by activating a switch of the system, etc.). Accordingly, in certain embodiments, reader device 120 will output a current (real time) sensor-derived analyte value (e.g., in numerical format), a current rate of analyte change (e.g., in the form of an analyte rate indicator such as an arrow pointing in a direction to indicate the current rate), and analyte trend history data based on sensor readings acquired by and stored in memory of sensor control device 102 (e.g., in the form of a graphical trace). Additionally, an on-skin or sensor temperature reading or measurement may be communicated from sensor control device 102 with each data transmission. The temperature reading or measurement, however, may be used in conjunction with a software routine executed by reader device 120 to correct or compensate the analyte measurement output to the user by reader device 120, instead of or in addition to actually displaying the temperature measurement to the user.

In many example embodiments, the manufacturer of sensor control device 102 will also be the entity that provides the software of sensor interface application 232. The manufacturer of sensor control device 102 may not, however, also be the manufacturer of reader device 120, such as in those cases where reader device 120 is a smart phone. The user would download and install sensor interface application 232 on the smart phone to provide the functionality for interfacing with sensor control device 102 and for performing proprietary processing to the data received from sensor control device 102. While sensor interface application 232 can perform user interface functions as well, e.g., interface with the user, present measurement results to the user, and accept commands from the user, in certain embodiments it may be desirable for the user to download and install a separate user interface application 234, provided by a third party, that performs the user interface functions and operates in conjunction with sensor interface application 232.

Example Embodiments of Authenticating and Interfacing Between Applications

Sensor interface application 232 can be programmed to operate with third-party applications in a variety of settings. This can provide the user with freedom to select the user interface that he or she deems most suitable from a number of different user interface applications that might be available, e.g., in an applications store. However, the provider of sensor control device 102 and/or sensor interface application 232 may have reason to restrict those user interface applications 234 that can operate with sensor interface application 232. Such restriction can enable the provider to ensure that only those user interface applications that have met certain quality standards, e.g., verified through rigorous testing, are capable of accessing the data collected by sensor control device 102. The provider may have other standards of design, performance, and/or aesthetics that must be met to help ensure that the user has a satisfactory experience using sensor control device 102.

Regardless of the provider's reasons, however, functionality is needed to act as a gateway for deciding which applications should or should not be allowed to operate with sensor interface application 232. Accordingly, embodiments are provided herein that allow sensor interface application 232 to authenticate a third-party user interface application 234 and determine if that user interface application 234 is authorized to access the data collected by sensor control device 102 (through sensor interface application 232) and, if so, to what types of collected data access should be given.

In many embodiments, system 100 can maintain a compilation of approved third-party applications that are allowed to operate with sensor interface application 232. In some embodiments, this compilation is stored locally in any memory of the device on which sensor interface application 232 operates (e.g., reader device 120), for example, as a compilation 236 of approved applications as depicted in FIG. 2B. In other embodiments, this compilation is stored in a database located remotely from the device, for example, as a registration database 181 associated with trusted computer system 180 that is located remotely from reader device 120 and sensor control device 102. Compilation 236 can be any machine-readable information about applications that are approved for use including, but not limited to, a data structure, a table, a list, a database, an array, a compilation of machine readable instructions (e.g., a software routine), a hardware lookup table, and so forth. When stored locally (e.g., on reader device 120), compilation 236 can be accessed directly to determine whether a particular user interface application 234 is present within the list and/or indicated as being approved for use. When stored remotely, registration database 181 can be accessed by the device executing application 232 using, e.g., an Internet connection or the like.

Figure 3A:
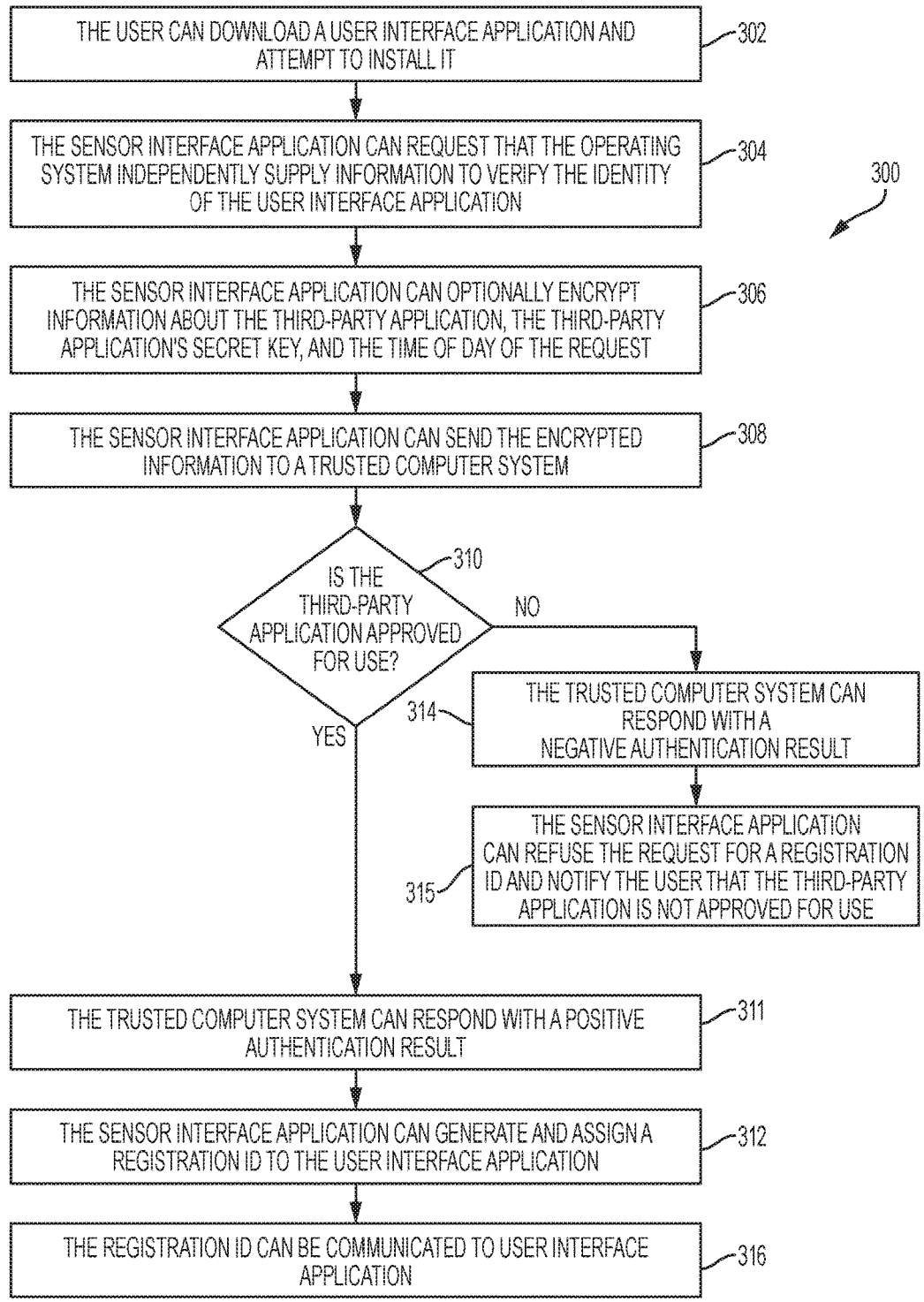
FIG. 3A is a block diagram depicting an example method of authenticating a third-party user interface application by reference to a remote registration database.

FIG. 3A is a block diagram depicting an example method 300 of authenticating a third-party user interface application 234 operating on a smart phone by reference to a remote registration database 181. In this embodiment, sensor interface application 232 has already been installed and is currently running. At 302, the user downloads user interface application 234 and attempts to install it. During the install process, user interface application 234 requests a registration identifier (ID) from sensor interface application 232. The request can include identifying information about user interface application 234, such as the name of the application, the size of the application, the version of the application, an error correction code (CRC), and/or the time of day that the request was generated, or any combination thereof. The request can also include a secret code (e.g., a public key used in asymmetric cryptography) that is associated only with that particular application name and/or version.

The registration ID is a string of characters that can act as a passcode for obtaining access to sensor interface application 232, either by direct transmission of the registration ID itself, or by use of the registration ID as a key (e.g., a private key used in asymmetric cryptography). Without the correct registration ID, user interface application 234 will not be allowed to operate with sensor interface application 232. In certain embodiments, the registration ID is a lengthy random or pseudorandom string of characters and can be unique to the particular instance of user interface application 234 and sensor interface application 232. In other words, although another reader device 120 may also be running the same versions of sensor interface application 232 and user interface application 234, that other reader device 120 would use a different registration ID because that pairing is being executed on a physically different reader device 120. Those of skill in the art will readily recognize that numerous variations to the scheme exist, including using a common registration ID for all applications operating with a particular sensor interface application 232, a common registration ID for all instances where a particular version of sensor interface application 232 operates with a particular version of user interface application 234 regardless of what physical device those instances occur on, and so forth.

At 304, sensor interface application 232 consults with operating system 230 by requesting that operating system 230 independently supply information to be used to verify that user interface application 234 is the same application that it purports to be. The information used to verify the identity of the user interface application 234 can be chosen as desired, and can include the name of the application, the size of the application, the version of the application, an error correction code (CRC) for the application, and so forth. The amount of information used to verify the identity of user interface application 234 can vary, and can be chosen as a result of a balance between requiring too much information that makes the maintenance of an up-to-date compilation 236 of approved applications overly burdensome, and requiring too little information that makes it relatively easy for the provider of an unapproved user interface application 234 to impersonate an approved application 234. If the information provided by operating system 230 matches that information supplied by user interface application 234 in its request for a registration ID, then sensor interface application 232 can treat the identity of user interface application 234 has been verified and can proceed with authenticating whether that application 234 is approved for use.

At 306, sensor interface application 232 can optionally encrypt (e.g., using a private key) the information about user interface application 234, the user interface application's secret key, and the time of day of the request and, at 308, sends the encrypted information to trusted computer system 180, e.g., over a secure Internet connection 142.

At 310, trusted computer system 180 determines if user interface application 234 is approved for use with sensor interface application 232. In many embodiments, this can occur by comparing all or part of the received encrypted information about application 234 with the corresponding information contained within registration database 181 to determine if that particular user interface application 234 is approved. Trusted computer system 180 can also determine if the time of day information, or other timestamp taken from the request, remains valid and has not expired.

If user interface application 234 is present within registration database 181 and indicated as being approved for use, and if the time of day information is recent enough, then trusted computer system 180 will respond to reader device 120 with a positive authentication result, i.e., an indication that user interface application 234 is approved for use, at 311. If user interface application 234 is not present within registration database 181, e.g., user interface application 234 is unknown or is a version that is too old or has not yet been approved, or if the time of day information indicates that the request is too old (e.g., which may suggest a replicated request), then trusted computer system 180 will respond to reader device 120 with a negative authentication result at 314, i.e., an indication that user interface application 234 is not approved.

Upon receiving a negative authentication result from trusted computer system 180, sensor interface application 232 can refuse the request for a registration ID and notify the user that user interface application 234 is not approved for use with either sensor interface application 232 or sensor control device 102, as indicated at 315.

Upon receiving a positive authentication result from trusted computer system 180, at 312, sensor interface application 232 can generate and assign a registration ID to the third party user interface application 234. The registration ID can then be communicated to user interface application 234 at 316. User interface application 234 can then include the assigned registration ID with every call (e.g., application program interface (API) call) of sensor interface application 232. Upon being called, sensor interface application 232 can verify the registration ID prior to responding.

In certain cases, it may be desirable to restrict the user interface application's access to only certain subsets of the available data and/or restrict the user interface application's functionality. The embodiments described herein can enable sensor interface application 232 to recognize these restrictions. In some embodiments, user interface application 234 may only be approved to display historical analyte data and not current analyte data, for example, if that user interface application 234 is not fully capable of communicating alarms to the user when current analyte levels move outside of acceptable ranges (e.g., if a user has a hypoglycemic or hyperglycemic condition, an impending hyperglycemic condition or an impending hypoglycemic condition, etc.). In some embodiments, user interface application 234 may not be approved to request that sensor control device 102 communicates updated analyte measurements (e.g., an on-demand request). Any number of reasons could serve as motivation to grant only limited data access and the data to which access is restricted is entirely up to the system provider.

Figure 3B:
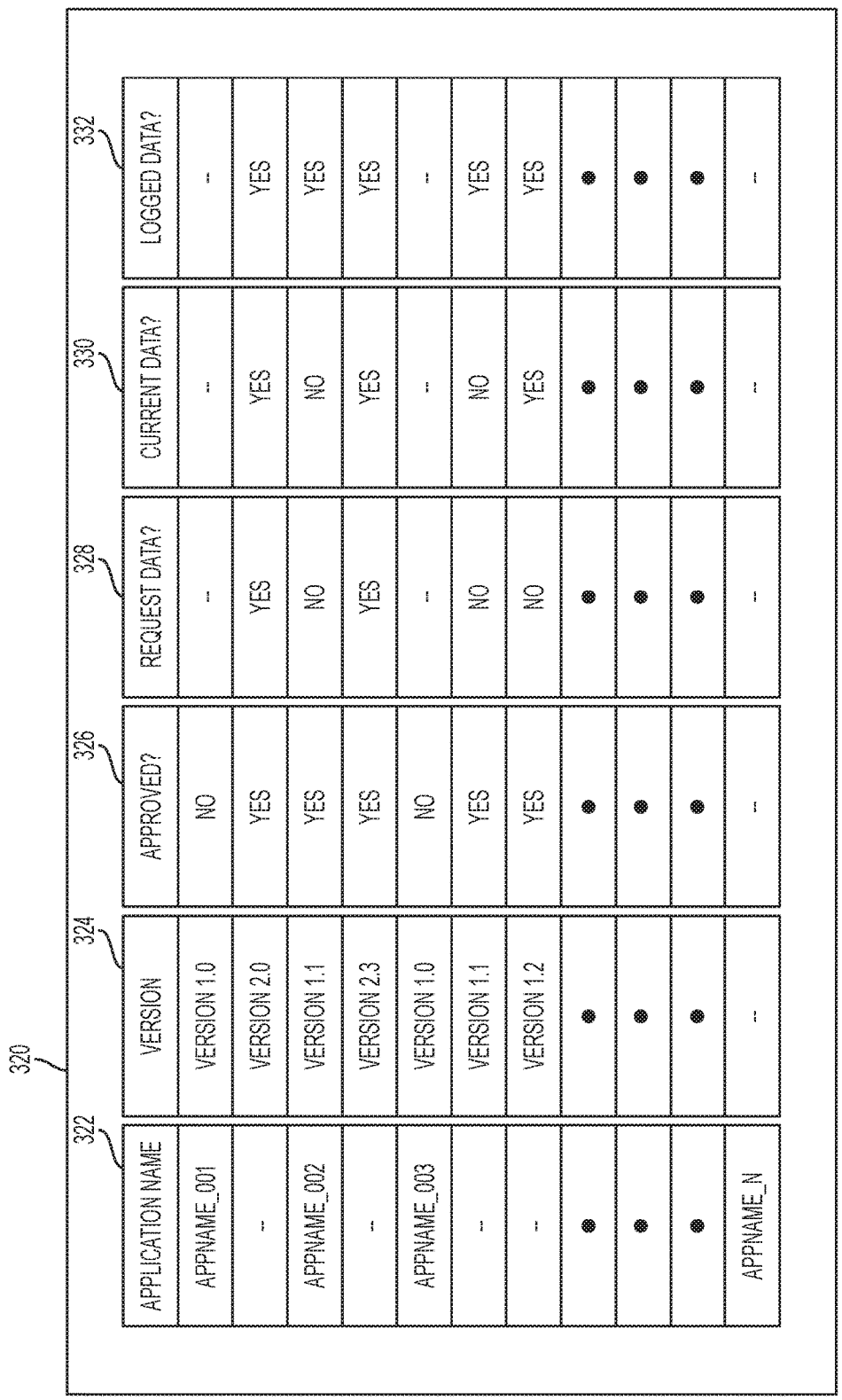
FIG. 3B is a block diagram depicting an example embodiment of a compilation of information relating to various third-party applications and their level of approved functionality.

FIG. 3B is a block diagram depicting an example embodiment of a compilation 320 of information relating to various third-party applications and their level of approved functionality that can be used with registration database 181 or as local compilation 236. Compilation 320 is depicted here in human readable form, and it should be noted that in most embodiments, the information shown here would instead be implemented in machine-readable form. For each user interface application 234, compilation 320 can include an associated indication of the level of functionality and types of data to which the third-party application will have access.

Here, a first partition (e.g., column) 322 includes the various application names (or other identifiers) of which the provider of sensor interface application 232 is aware. Partition 324 includes the various versions that are available for each application name. For each version, indications of the level of functionality and data access are provided in partitions 326, 328, 330, and 332. Partition 326 contains an indication of whether each particular version is or is not approved for use with sensor interface application 232. If a version is not approved, then, in this embodiment, that version will have no approved functionality for data access. However, in other embodiments limited access could be granted to unapproved software applications. Partition 328 includes an indication whether each version is approved to initiate a sensor measurement and/or transmission of current analyte data. Partition 330 includes an indication whether each version is approved to display the user's current analyte measurement. Partition 332 includes an indication whether each version is approved to display historical (i.e., not current) analyte data of the user.

In the embodiment described with respect to FIG. 3A, trusted computer system 180 can reference compilation 320 within registration database 181 and determine the level of functionality and access for the third-party application. If the application is not present, then trusted computer system 180 can take a default action which can include allowing no functionality or access, or granting limited functionality or access, such as granting access to historical analyte data. The authentication result that is conveyed to reader device 120 can contain a bit string that indicates the level of approved functionality and access for the particular user interface application 234.

In embodiments where compilation 320 of approved applications is instead stored locally on reader device 120, the operation of method 300 will remain generally the same as described with respect to FIG. 3A, except that sensor interface application 232 will not have to encrypt a request at 306 and send the request over the Internet at 308, as it will already have direct access to compilation 320. It may be desirable for sensor interface application 232 to check with trusted computer system 180 to determine if any updates to compilation 320 exist prior to determining whether user interface application 234 is approved for use. Any updates can be transmitted over the Internet from trusted computer system 180 and the information within compilation 320 can be revised and appended as needed.

For user interface applications 234 that are approved for use with sensor interface application 232 in the monitoring of the user's current analyte level, there may be instances where critical events are detected that must be communicated to the user (which in most cases will be the user of sensor control device 102). These critical events can include changes in the current analyte level that exceed a predetermined range (e.g., a hypoglycemic or hyperglycemic condition), changes in the rate of change of the current analyte level that might indicate risk to the user, a potential adverse condition associated with the operation of the sensor, and/or a potential sensor stability degradation condition, and others. These critical events can be detected by sensor control device 102 or sensor interface application 232. These critical events may require the user to take action (e.g., administration of insulin), a component of system 100 to temporarily shut down (automatically without notification to the user, or after notifying the user), or a display of the monitored analyte level to be temporarily disabled.

Accordingly, it is important that an indication of the critical event, for example, in the form of a warning, alarm, or error, be communicated to the user. When operating with a third-party user interface application 234, sensor interface application 232 may require confirmation that the critical event was communicated in some form to the user.

Figure 4:
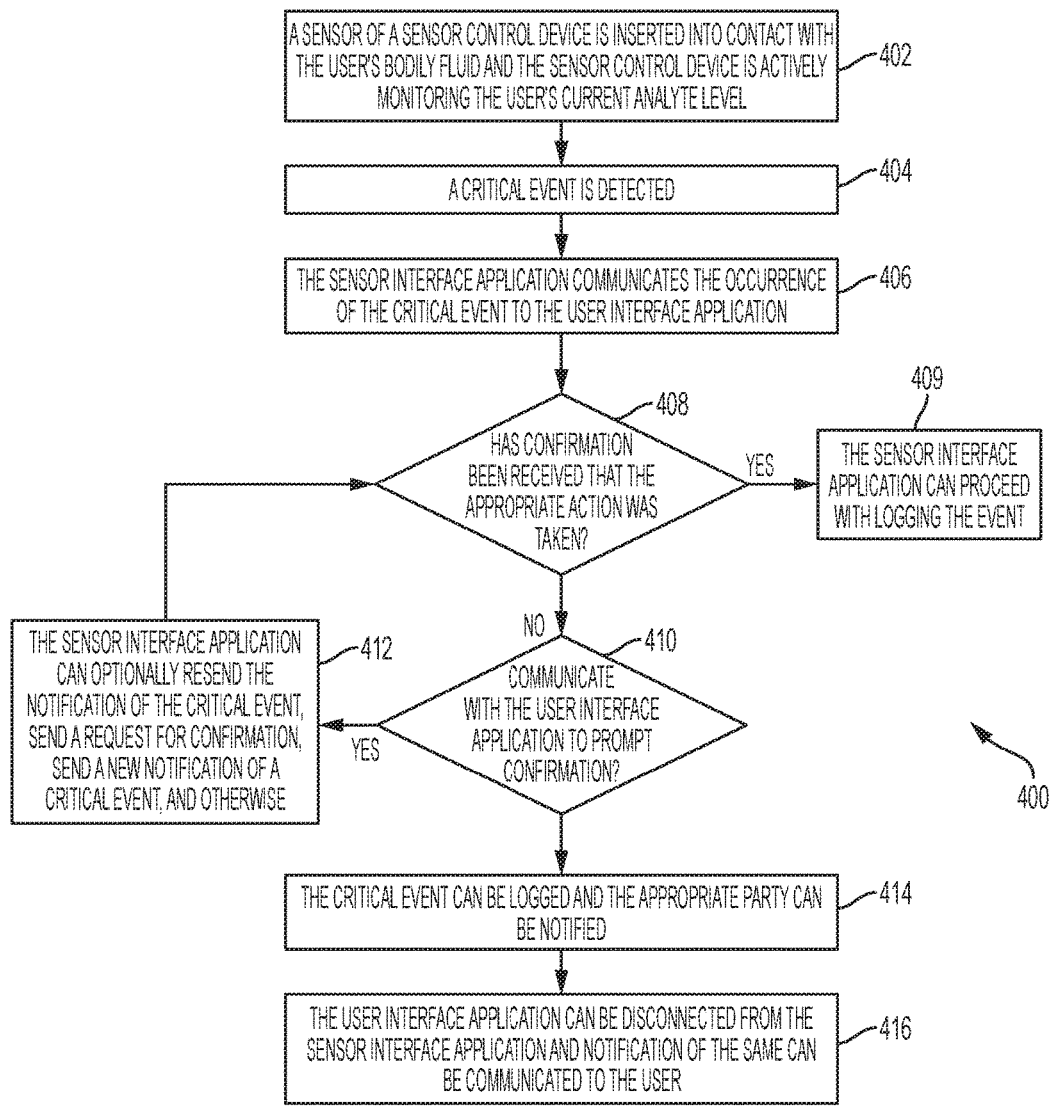
FIG. 4 is a block diagram depicting an example embodiment of a method of obtaining confirmation for a sensor interface application that a user interface application has communicated a critical event to a user.

FIG. 4 is a block diagram depicting an example embodiment of a method 400 of obtaining confirmation for the sensor interface application 232 that a user interface application 234 has indeed communicated the critical event to the user. At 402, sensor 104 of sensor control device 102 has been inserted into contact with the user's bodily fluid and sensor control device 102 is actively monitoring the user's current analyte level. At 404, a critical event is detected (examples of which are described above). At 406, sensor interface application 232 communicates the occurrence of the critical event to user interface application 234 (alternatively, sensor interface application 232 might independently monitor for the occurrence of a critical event in parallel with user interface application 234 such that no communication of the occurrence of the event may be required).

At 408, sensor interface application 232 monitors for confirmation from user interface application 234 that the appropriate action was taken, which may include causing the display of the critical event to the user and receiving confirmation from the user that the notification has been received. If confirmation is received from user interface application 234, then sensor interface application 232 may proceed with logging the event at 409 and optionally (e.g., in the case of a device error) communicating the event to the manufacturer.

If no confirmation is received after a predetermined time period, sensor interface application 232 determines whether to communicate with user interface application 234 again to prompt confirmation at 410. This determination can be implemented simply in the form of a software instruction to prompt confirmation again or not. If sensor interface application 232 is to make another communication, then at 412 sensor interface application 232 can optionally resend the notification of the critical event to user interface application 234, send a request for confirmation, send a new notification of a critical event, or any combination thereof, and again monitor for receipt of the confirmation at 408. If no confirmation is received again, then the routine proceeds to step 410 again, which can include a predetermined limit on the number of repeated tries 412 to avoid an unlimited loop.

If no confirmation is ever received, then the critical event is logged at 414 and the provider of sensor interface application 232 (and/or the manufacturer of sensor control device 102 or other appropriate party) is notified. At 416, the user interface application 234 can be disconnected from sensor interface application 232 and notification of the same can be communicated to the user. That instance of sensor interface application 232 can be programmed to refuse further attempts to connect user interface application 234 until a positive notification is received from trusted computer system 180 that access should again be granted.

For all embodiments described herein, should it be detected or learned that a particular user interface application 234 is not operating correctly, or that it contains a flaw, or other motivation arises to cast doubt on the functionality of that user interface application 234, then trusted computer system 180 can remotely cause the disconnection of that application from sensor interface application 232. Trusted computer system 180 can send a notification to sensor interface application 232 over any of the available communication services of reader device 120, such as the cellular telephony network or the local wireless Internet (e.g. Wi-Fi). Upon receiving this notification, sensor interface application 232 will read the notification and determine what course of action to take, such as performing a full disconnection of the third-party application or limiting that third-party application's functionality or data access privileges, such as already described herein.

Referring back to FIG. 2B, a number of different user interface applications to 234-1, 234-2, and 234-3 are depicted. Because each of these user interface applications 234-1, 234-2, and 234-3 can be collecting and/or maintaining different types and values of data about the user or an aspect of the user's diabetes monitoring regimen, it can be required that each and every one of these user interface applications 234-1, 234-2, and 234-3 utilize sensor interface application 232 as a common source for all such data. This may be as a condition to gaining approval for operation with sensor interface application 232, or it (the restriction of access to data) may be used as a way to maintain on-going or continuous control over which user interface applications 234 can operate with sensor interface application 232.

For example, user interface application 234 may estimate a recommended insulin dose and is approved for use in certain parts of the world, but it is not approved by the FDA for use in the USA. Sensor interface application 232 can refuse to supply analyte date to that user interface application 234, possibly with the assistance of GPS data supplied by GPS hardware of reader device 120 to monitor whether reader device 120 is currently in the USA. By way of another example, the provider of sensor interface application 232 may be alerted that a particular user interface application 234 contains or is susceptible to an error that causes the application 234 to give an incorrect insulin dose recommendation, in which case that application 234 could be blocked from access to the analyte data until such time as the error is resolved, e.g., a new version is downloaded.

Sensor interface application 232 can also capture information coming from any one of user interface applications 234-1, 234-2, and 234-3 and share that information with any other one of a user interface applications 234-1, 234-2, and 234-3. In this manner, sensor interface application 232 can be fully informed as to all aspects of the user's diabetes monitoring regimen and can share any portion of that information with any of the user interface applications 234-1, 234-2, and 234-3 operating on a reader device 120, as well as those that may be installed at a later time.

Example Embodiments of Controlling the Display of Analyte Data and Critical Events Also provided herein are example embodiments of software and methods for controlling the display of analyte measurement results and critical events by one or more applications running on a reader device implemented as, e.g., a smart phone (or other mobile communication device) or other electronics assembly that can execute software applications.

Conventional reader devices that are dedicated devices, e.g., devices whose primary function is the monitoring of a user's analyte level, are designed with features that ensure that the user's current analyte data is displayed expeditiously and for the appropriate amount of time without interruption. The occurrence of critical events can be communicated to the user directly and confirmation that the user has understood the communication can be obtained. However, the performance of similar functions on non-dedicated devices, such as smart phones, is more complex since those devices are not designed with the execution of a diabetes monitoring regimen as the primary function. For example, with a smart phone, the display of analyte results could be interrupted by the user sending the diabetes monitoring application into an inactive state (in the background) by actuating a home screen button, or by the receipt of a phone call, or the receipt of a text message, and so forth. This can be problematic if a critical event has occurred and the user has not had sufficient time to read and/or interpret a notification of the critical event.

Also, the re-display of the older analyte results can occur when the diabetes monitoring application is recalled into the active state (the foreground) of the smart phone. This can be problematic if that particular display of analyte measurements is intended to represent the user's "current" analyte level, as the passage of a predetermined time period may have disqualified those older analyte results from being representative of the "current" level. The time period during which the received data is considered current, i.e., the duration of the current data age timer or the duration of a current data age window, is dependent upon the needs of each individual application. In some embodiments received data may be current for a few seconds or a minute, while in other embodiments receive data may be current for 5 minutes, 10 minutes, 15 minutes, an hour, and so forth.

Figure 5:
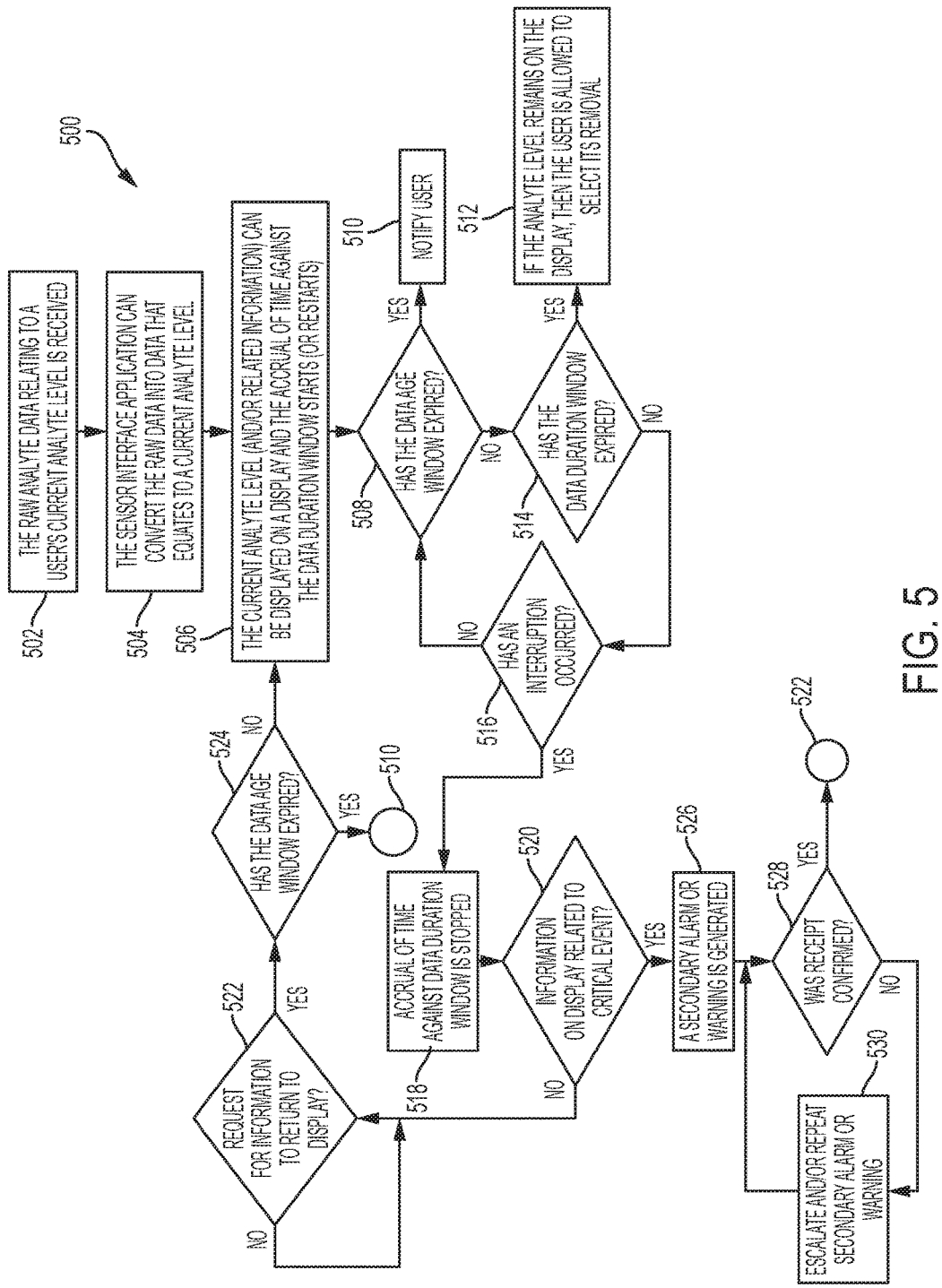
FIG. 5 is a block diagram depicting an example embodiment of a method of displaying measured analyte results on a smart phone type reader device.

FIG. 5 is a block diagram depicting an example embodiment of a method 500 of displaying measured analyte results on a smart phone type reader device 120 that can address the aforementioned concerns. At 502, raw analyte data relating to a user's current analyte level is received at reader device 120 from sensor control device 102. Upon receipt, reader device 120 may take action to track the amount of time that has passed since receipt in order to determine when the data is no longer considered to be current. The received data from sensor control device 102 may contain a timestamp that reader device 120 can use in this regard. Alternatively, reader device 120 can record the time of receipt, or even initiate a current data age timer, the expiration of which will indicate that the received data is no longer current.

At 504, sensor interface application 232 can process the received raw data using one or more algorithms to convert the raw data into data that equates to the user's current analyte level. The current analyte level is then displayed on display 122 of reader device 120 at 506. This can optionally occur after sensor interface application 232 confirms that the current analyte level data is still current, i.e., within the current data age window. The display can occur after sensor interface application 232 has conveyed the current analyte level to a third party user interface application 234, if such an application has been installed. Otherwise sensor interface application 232 can cause the display of the current analyte level directly.

Each of the following steps can be performed by processing hardware 206 of reader device 120, while executing sensor interface application 232 and any user interface application 234 that may be employed. Instructions for carrying out these steps can come from or otherwise be associated with any of applications 232 or 234.

At 508, it is assessed whether the current data age window has expired (e.g., is the current analyte level still current?). If it has expired, then the user is notified at 510. The notification can entail informing the user that the current analyte level is no longer current, or is historical, while either continuing to display that analyte level or removing it from display 122. If the analyte level remains on display 122, then the user is allowed to select its removal at 512. In some embodiments, the notification is provided by changing the display from a current analyte level view to a historical view, or log view, with the most recent current analyte level displayed as a new entry in the log of historical levels.

Referring back to step 508, if the current data age window has not expired, then it is assessed whether the current analyte level has been displayed for a minimum duration of time at 514. The minimum duration of time, also referred to herein as a display duration window, can help ensure that the user's current analyte level has been displayed long enough for the user to comprehend its value. The minimum duration of time can be predetermined and can have a value according to the needs of the individual application, for example, 3 seconds, 5 seconds, 10 seconds, and so forth. To compute whether the minimum duration of time has been reached, a timer can be initiated upon the display of current analyte level, or the time at which the current analyte level was first displayed can be recorded and calculations can be iteratively performed to determine whether the display duration window has been reached. If the current analyte level has been displayed for the minimum duration of time, then the process can proceed to step 512.

If the minimum duration of time has not been satisfied, then an assessment is made at 516 if an interruption has occurred in the display of the current analyte level. One example of an interruption is the inactivation of the application responsible for displaying the current analyte level, such as when a user sends the application to the background by pressing a home screen button on the smart phone. If no interruption has occurred, then the process proceeds back to step 508 and continues. If an interruption has occurred, then, at 518, the data duration window is stopped (the time accruing against the window thereafter is not counted), or the time at which the interruption occurred is recorded, or other action is taken to ensure that the duration of time that the current analyte level is not on display 122 is not counted against the data display window.

Next, an assessment is made as to whether the current analyte level that was displayed is related to a critical event (or alternatively, whether a critical event was being displayed) at 520. If unrelated to a critical event, then an assessment is made at 522 whether a request has been received to bring the current analyte level back to display 122 (e.g., the user has reactivated the application and attempted to bring it to the foreground). If not, then the process continues to monitor for a request to return the current analyte level to display 122. If a request has been received, then an assessment is made at 524 whether the current analyte level is still current and valid (e.g., whether the data duration window has expired) and if so, the current analyte level is returned to the display at 506, at which point the data duration window is restarted. If the current analyte level is no longer current, then the process proceeds to step 510.

Referring back to assessment step 520, if it is determined that the current analyte level that was being displayed is related to a critical event, then at 526, a secondary alarm or warning is generated as the current analyte level (or critical event itself) has not yet been displayed to the user for a sufficient amount of time. The secondary alarm or warning can be in any desired form, such as a visual notification, tactile notification (e.g., vibration), or audible notification (e.g., an audible alarm, bell, etc.). In some embodiments, the secondary alarm is a text message that is transmitted to the smart phone. In other embodiments, the secondary alarm can be an actual telephone call placed by the provider of sensor interface application 232 or the service provider, or can be a forced visual notification similar to a calendar reminder.

At 528 and assessment is made whether the user has confirmed receipt of the secondary alarm or warning. If so, then the process can return to step 522. If not, then in some embodiments it may be desirable to escalate the secondary alarm or warning to increase the likelihood of obtaining the attention of the user. This escalation step is depicted at 530 and can entail a relative increase in the level of notification provided to the user by the secondary alarm or warning. For instance, if a visual indication was forced as part of step 526, then the escalation step 530 can include forcing the visual indication a second time and also providing a tactile or audible notification. As another example, if a visual and audible notification was provided as part of step 526, then the escalation step 530 can include again providing the visual and audible notification accompanied by a text message. The process will then continue back to step 528 to determine if confirmation from the user is obtained. The process can continue in this loop as many times as desired, but in many embodiments a practical limit to the number of repeat secondary alarms will be desirable.

It should be noted that, while methods 300, 400, and 500 described herein can be implemented in their entirety, these methods are intended to describe numerous features and routines that can be included in a diabetes monitoring software. Accordingly, it should be understood (and those of ordinary skill in the art will readily recognize) that a number of different subsets of steps shown and/or described with respect to FIGS. 3A, 4, and 5 can be implemented, or claimed, while still achieving the benefits of the described methods 300 and 400. This can extend to particular combinations of steps that are in applied but not explicitly shown or described with respect to FIGS. 3A, 4, and 5, as the number of possible permutations is too voluminous to be described herein.

US Patent Application Publ. No. 2011/0213225 (the '225 Publication) generally describes components of an in vivo-based analyte monitoring system that are suitable for use with the system, device, and method embodiments described herein. The '225 Publication is incorporated by reference herein in its entirety for all purposes.

Sensor Configurations

Analytes that may be monitored with system 100 include, but are not limited to, acetyl choline, amylase, bilirubin, cholesterol, chorionic gonadotropin, glycosylated hemoglobin (HbAlc), creatine kinase (e.g., CK-MB), creatine, creatinine, DNA, fructosamine, glucose, glucose derivatives, glutamine, growth hormones, hormones, ketones, ketone bodies, lactate, oxygen, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In embodiments that monitor more than one analyte, the analytes may be monitored at the same or different times with a single sensor or with a plurality of sensors which may use the same electronics (e.g., simultaneously) or with different electronics of the sensor control device.

Analyte sensor 104 may include an analyte-responsive enzyme to provide a sensing element. Some analytes, such as oxygen, can be directly electrooxidized or electroreduced on sensor 104, and more specifically at least on a working electrode (not shown) of a sensor 104. Other analytes, such as glucose and lactate, require the presence of at least one electron transfer agent and/or at least one catalyst to facilitate the electrooxidation or electroreduction of the analyte. Catalysts may also be used for those analytes, such as oxygen, that can be directly electrooxidized or electroreduced on the working electrode. For these analytes, each working electrode includes a sensing element proximate to or on a surface of a working electrode. In many embodiments, a sensing element is formed near or on only a small portion of at least a working electrode.

Each sensing element includes one or more components constructed to facilitate the electrochemical oxidation or reduction of the analyte. The sensing element may include, for example, a catalyst to catalyze a reaction of the analyte and produce a response at the working electrode, an electron transfer agent to transfer electrons between the analyte and the working electrode (or other component), or both.

A variety of different sensing element configurations may be used. In certain embodiments, the sensing elements are deposited on the conductive material of a working electrode. The sensing elements may extend beyond the conductive material of the working electrode. In some cases, the sensing elements may also extend over other electrodes, e.g., over the counter electrode and/or reference electrode (or counter/ reference where provided). In other embodiments, the sensing elements are contained on the working electrode, such that the sensing elements do not extend beyond the conductive material of the working electrode. In some embodiments a working electrode is configured to include a plurality of spatially distinct sensing elements. Additional information related to the use of spatially distinct sensing elements can be found in U.S. Provisional Application No. 61/421,371, entitled "Analyte Sensors with Reduced Sensitivity Variation," which was filed on Dec. 9, 2010, and which is incorporated by reference herein in its entirety and for all purposes.

The terms "working electrode", "counter electrode", "reference electrode" and "counter/reference electrode" are used herein to refer to conductive sensor components, including, e.g., conductive traces, which are configured to function as a working electrode, counter electrode, reference electrode or a counter/reference electrode respectively. For example, a working electrode includes that portion of a conductive material, e.g., a conductive trace, which functions as a working electrode as described herein, e.g., that portion of a conductive material which is exposed to an environment containing the analyte or anlaytes to be measured, and which, in some cases, has been modified with one or more sensing elements as described herein. Similarly, a reference electrode includes that portion of a conductive material, e.g., conductive trace, which function as a reference electrode as described herein, e.g., that portion of a conductive material which is exposed to an environment containing the analyte or analytes to be measured, and which, in some cases, includes a secondary conductive layer, e.g., a Ag/AgCl layer. A counter electrode includes that portion of a conductive material, e.g., conductive trace which is configured to function as a counter electrode as described herein, e.g., that portion of a conductive trace which is exposed to an environment containing the analyte or anlaytes to be measured. As noted above, in some embodiments, a portion of a conductive material, e.g., conductive trace, may function as either or both of a counter electrode and a reference electrode. In addition, "working electrodes", "counter electrodes", "reference electrodes" and "counter/reference electrodes" may include portions, e.g., conductive traces, electrical contacts, or areas or portions thereof, which do not include sensing elements but which are used to electrically connect the electrodes to other electrical components.

Sensing elements that are in direct contact with the working electrode, e.g., the working electrode trace, may contain an electron transfer agent to transfer electrons directly or indirectly between the analyte and the working electrode, and/or a catalyst to facilitate a reaction of the analyte. For example, a glucose, lactate, or oxygen electrode may be formed having sensing elements which contain a catalyst, including glucose oxidase, glucose dehydrogenase, lactate oxidase, or laccase, respectively, and an electron transfer agent that facilitates the electrooxidation of the glucose, lactate, or oxygen, respectively.

In other embodiments the sensing elements are not deposited directly on the working electrode, e.g., the working electrode trace. Instead, the sensing elements may be spaced apart from the working electrode trace, and separated from the working electrode trace, e.g., by a separation layer. A separation layer may include one or more membranes or films or a physical distance. In addition to separating the working electrode trace from the sensing elements, the separation layer may also act as a mass transport limiting layer and/or an interferent eliminating layer and/or a biocompatible layer.

In certain embodiments which include more than one working electrode, one or more of the working electrodes may not have corresponding sensing elements, or may have sensing elements that do not contain one or more components (e.g., an electron transfer agent and/or catalyst) needed to electrolyze the analyte. Thus, the signal at this working electrode may correspond to background signal which may be removed from the analyte signal obtained from one or more other working electrodes that are associated with fully-functional sensing elements by, for example, subtracting the signal.

In certain embodiments, the sensing elements include one or more electron transfer agents. Electron transfer agents that may be employed are electroreducible and electrooxidizable ions or molecules having redox potentials that are a few hundred millivolts above or below the redox potential of the standard calomel electrode (SCE). The electron transfer agent may be organic, organometallic, or inorganic. Examples of organic redox species are quinones and species that in their oxidized state have quinoid structures, such as Nile blue and indophenol. Examples of organometallic redox species are metallocenes including ferrocene. Examples of inorganic redox species are hexacyanoferrate (III), ruthenium hexamine, etc. Additional examples include those described in U.S. Pat. Nos. 6,736,957, 7,501,053 and 7,754,093, the disclosures of each of which are incorporated herein by reference in their entirety.

In certain embodiments, electron transfer agents have structures or charges which prevent or substantially reduce the diffusional loss of the electron transfer agent during the period of time that the sample is being analyzed. For example, electron transfer agents include but are not limited to a redox species, e.g., bound to a polymer which can in turn be disposed on or near the working electrode. The bond between the redox species and the polymer may be covalent, coordinative, or ionic. Although any organic, organometallic or inorganic redox species may be bound to a polymer and used as an electron transfer agent, in certain embodiments the redox species is a transition metal compound or complex, e.g., osmium, ruthenium, iron, and cobalt compounds or complexes. It will be recognized that many redox species described for use with a polymeric component may also be used, without a polymeric component.

Embodiments of polymeric electron transfer agents may contain a redox species covalently bound in a polymeric composition. An example of this type of mediator is poly (vinylferrocene). Another type of electron transfer agent contains an ionically-bound redox species. This type of mediator may include a charged polymer coupled to an oppositely charged redox species. Examples of this type of mediator include a negatively charged polymer coupled to a positively charged redox species such as an osmium or ruthenium polypyridyl cation.

Another example of an ionically-bound mediator is a positively charged polymer including quaternized poly (4-vinyl pyridine) or poly(l-vinyl imidazole) coupled to a negatively charged redox species such as ferricyanide or ferrocyanide. In other embodiments, electron transfer agents include a redox species coordinatively bound to a polymer. For example, the mediator may be formed by coordination of an osmium or cobalt 2,2'-bipyridyl complex to poly(l-vinyl imidazole) or poly(4-vinyl pyridine).

Suitable electron transfer agents are osmium transition metal complexes with one or more ligands, each ligand having a nitrogen-containing heterocycle such as 2,2'-bipyridine, 1,10-phenanthroline, 1-methyl, 2-pyridyl biimidazole, or derivatives thereof. The electron transfer agents may also have one or more ligands covalently bound in a polymer, each ligand having at least one nitrogen-containing heterocycle, such as pyridine, imidazole, or derivatives thereof. One example of an electron transfer agent includes (a) a polymer or copolymer having pyridine or imidazole functional groups and (b) osmium cations complexed with two ligands, each ligand containing 2,2'-bipyridine, 1,10-phenanthroline, or derivatives thereof, the two ligands not necessarily being the same. Some derivatives of 2,2'-bipyridine for complexation with the osmium cation include but are not limited to 4,4'-dimethyl-2,2'-bipyridine and mono-, di-, and polyalkoxy-2,2'-bipyridines, including 4,4'-dimethoxy-2,2'-bipyridine. Derivatives of 1,10-phenanthroline for complexation with the osmium cation include but are not limited to 4,7-dimethyl-1,10-phenanthroline and mono, di-, and polyalkoxy-1,10-phenanthrolines, such as 4,7-dimethoxy-1,10-phenanthroline. Polymers for complexation with the osmium cation include but are not limited to polymers and copolymers of poly(l-vinyl imidazole) (referred to as "PVI") and poly(4-vinyl pyridine) (referred to as "PVP"). Suitable copolymer substituents of poly(l-vinyl imidazole) include acrylonitrile, acrylamide, and substituted or quaternized N-vinyl imidazole, e.g., electron transfer agents with osmium complexed to a polymer or copolymer of poly(l-vinyl imidazole).

Embodiments may employ electron transfer agents having a redox potential ranging from about −200 mV to about +200 mV versus the standard calomel electrode (SCE). The sensing elements may also include a catalyst which is capable of catalyzing a reaction of the analyte. The catalyst may also, in some embodiments, act as an electron transfer agent. One example of a suitable catalyst is an enzyme which catalyzes a reaction of the analyte. For example, a catalyst, including a glucose oxidase, glucose dehydrogenase (e.g., pyrroloquinoline quinone (PQQ) dependent glucose dehydrogenase, flavine adenine dinucleotide (FAD) dependent glucose dehydrogenase, or nicotinamide adenine dinucleotide (NAD) dependent glucose dehydrogenase), may be used when the analyte of interest is glucose. A lactate oxidase or lactate dehydrogenase may be used when the analyte of interest is lactate. Laccase may be used when the analyte of interest is oxygen or when oxygen is generated or consumed in response to a reaction of the analyte.

In certain embodiments, a catalyst may be attached to a polymer, cross linking the catalyst with another electron transfer agent, which, as described above, may be polymeric. A second catalyst may also be used in certain embodiments. This second catalyst may be used to catalyze a reaction of a product compound resulting from the catalyzed reaction of the analyte. The second catalyst may operate with an electron transfer agent to electrolyze the product compound to generate a signal at the working electrode. Alternatively, a second catalyst may be provided in an interferent-eliminating layer to catalyze reactions that remove interferents.

In certain embodiments, the sensor works at a low oxidizing potential, e.g., a potential of about +40 mV vs. Ag/AgCl. These sensing elements use, for example, an osmium (Os)-based mediator constructed for low potential operation. Accordingly, in certain embodiments the sensing elements are redox active components that include: (1) osmium-based mediator molecules that include (bidente) ligands, and (2) glucose oxidase enzyme molecules. These two constituents are combined together in the sensing elements of the sensor.

A mass transport limiting layer (not shown), e.g., an analyte flux modulating layer, may be included with the sensor to act as a diffusion-limiting barrier to reduce the rate of mass transport of the analyte, for example, glucose or lactate, into the region around the working electrodes. The mass transport limiting layers are useful in limiting the flux of an analyte to a working electrode in an electrochemical sensor so that the sensor is linearly responsive over a large range of analyte concentrations and is easily calibrated. Mass transport limiting layers may include polymers and may be biocompatible. A mass transport limiting layer may provide many functions, e.g., biocompatibility and/or interferent-eliminating functions, etc. A mass transport limiting layer may be applied to an analyte sensor as described herein via any of a variety of suitable methods, including, e.g., dip coating and slot die coating.

In certain embodiments, a mass transport limiting layer is a membrane composed of crosslinked polymers containing heterocyclic nitrogen groups, such as polymers of polyvinylpyridine and polyvinylimidazole. Embodiments also include membranes that are made of a polyurethane, or polyether urethane, or chemically related material, or membranes that are made of silicone, and the like.

A membrane may be formed by crosslinking in situ a polymer, modified with a zwitterionic moiety, a non-pyridine copolymer component, and optionally another moiety that is either hydrophilic or hydrophobic, and/or has other desirable properties, in an alcohol-buffer solution. The modified polymer may be made from a precursor polymer containing heterocyclic nitrogen groups. For example, a precursor polymer may be polyvinylpyridine or polyvinylimidazole. Optionally, hydrophilic or hydrophobic modifiers may be used to "fine-tune" the permeability of the resulting membrane to an analyte of interest. Optional hydrophilic modifiers, such as poly (ethylene glycol), hydroxyl or polyhydroxyl modifiers, may be used to enhance the biocompatibility of the polymer or the resulting membrane.

A membrane may be formed in situ by applying an alcohol-buffer solution of a crosslinker and a modified polymer over the enzyme-containing sensing elements and allowing the solution to cure for about one to two days or other appropriate time period. The crosslinker-polymer solution may be applied over the sensing elements by placing a droplet or droplets of the membrane solution on the sensor, by dipping the sensor into the membrane solution, by spraying the membrane solution on the sensor, and the like. Generally, the thickness of the membrane is controlled by the concentration of the membrane solution, by the number of droplets of the membrane solution applied, by the number of times the sensor is dipped in the membrane solution, by the volume of membrane solution sprayed on the sensor, or by any combination of these factors. In order to coat the distal and side edges of the sensor, the membrane material may have to be applied subsequent to singulation of the sensor precursors. In some embodiments, the analyte sensor is dip-coated following singulation to apply one or more membranes. Alternatively, the analyte sensor could be slot-die coated wherein each side of the analyte sensor is coated separately. A membrane applied in the above manner may have any combination of the following functions: (1) mass transport limitation, i.e., reduction of the flux of analyte that can reach the sensing elements, (2) biocompatibility enhancement, or (3) interferent reduction.

In some embodiments, a membrane composition for use as a mass transport limiting layer may include one or more leveling agents, e.g., polydimethylsiloxane (PDMS). Additional information with respect to the use of leveling agents can be found, for example, in US Patent Application Publication No. US 2010/0081905, the disclosure of which is incorporated by reference herein in its entirety.

In some instances, the membrane may form one or more bonds with the sensing elements. The term "bonds" is intended to cover any type of an interaction between atoms or molecules that allows chemical compounds to form associations with each other, such as, but not limited to, covalent bonds, ionic bonds, dipole-dipole interactions, hydrogen bonds, London dispersion forces, and the like. For example, in situ polymerization of the membrane can form crosslinks between the polymers of the membrane and the polymers in the sensing elements. In certain embodiments, crosslinking of the membrane to the sensing element facilitates a reduction in the occurrence of delamination of the membrane from the sensor.

Analyte sensors may be insertable into a vein, artery, or other portion of the body containing the analyte. In certain embodiments, analyte sensors may be positioned in contact with ISF or dermal fluid to detect the level of analyte, where the detected analyte level may be used to infer the user's glucose level in blood or interstitial tissue.

Embodiments include transcutaneous sensors and also wholly implantable sensors and wholly implantable assemblies in which a single assembly including the analyte sensor and electronics are provided in a sealed housing (e.g., hermetically sealed biocompatible housing) for implantation in a user's body for monitoring one or more physiological parameters.

In many instances entities are described herein as being coupled to other entities. It should be understood that the terms "coupled" and "connected" (or any of their forms) are used interchangeably herein and, in both cases, are generic to the direct coupling of two entities (without any non-negligible (e.g., parasitic) intervening entities) and the indirect coupling of two entities (with one or more non-negligible intervening entities). Where entities are shown as being directly coupled together, or described as coupled together without description of any intervening entity, it should be understood that those entities can be indirectly coupled together as well unless the context clearly dictates otherwise.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed is:

1. A method of monitoring an analyte level of a human with an in vivo analyte sensor and a mobile communication device, the method comprising:
downloading and installing, by a user, a first application onto the mobile communication device;
downloading and installing, by the user, a different second application onto the mobile communication device, wherein the first application is a sensor interface application and the second application is a user interface application;
receiving data, at the mobile communication device, from the in vivo analyte sensor;
processing the received data with the sensor interface application to generate data indicative of an analyte level of the human;
determining, by the sensor interface application, whether the user interface application is authorized by reference to a registration database;
granting, by the sensor interface application to the user interface application, if authorized, access to the data indicative of the analyte level of the human;
communicating the data indicative of the analyte level of the human from the sensor interface application to the user interface application;
causing, by the user interface application, display of the analyte level of the human on a display of the mobile communication device; and
if an indication is received, at the sensor interface application, that access of the user interface application to the data indicative of the analyte level of the human is to be removed,
then removing access of the user interface application to the data indicative of the analyte level of the human.

2. The method of claim 1, wherein the user interface application is a first user interface application adapted to cause display of the analyte level of the human on the display of the mobile communication device, and the sensor interface application also communicates with a second user interface application adapted to cause display of the analyte level of the human on the display of the mobile communication device.

3. The method of claim 2, further comprising the following steps performed by the sensor interface application:
causing the capture of data from either the first user interface application or the second user interface application; and
providing the captured data to the other of the first or second user interface applications.

4. The method of claim 1, further comprising the following steps performed by the sensor interface application:
determining that a critical event has occurred; and
providing an indication to the user interface application that the critical event has occurred.

5. The method of claim 4, further comprising:
if a confirmation was not received from the user interface application that a notification of the critical event was provided to the user, then requesting that the user interface application provide the notification to the user.

6. The method of claim 5, further comprising:
after requesting that the user interface application provide the notification, if a confirmation was not received from the user interface application that the notification was provided, then disconnecting the user interface application from the sensor interface application.

7. The method of claim 5, further comprising:
after requesting that the user interface application provide the notification, if a confirmation was not received from the user interface application that the notification was provided, then logging the critical event and sending an error message to a trusted computer system over the internet.

8. The method of claim 4, further comprising:
if a confirmation was not received from the user interface application that a notification of the critical event was provided to the user, then providing the indication to user interface application that the critical event has occurred a second time.

9. The method of claim 8, further comprising:
after providing the indication to the user interface application a second time, if a confirmation was not received from the user interface application that the notification was provided, then disconnecting the user interface application from the sensor interface application.

10. The method of claim 8, further comprising:
after providing the indication to the user interface application a second time, if a confirmation was not received from the user interface application that the notification was provided, then logging the critical event and sending an error message to a trusted computer system over the internet.

11. The method of claim 4, wherein the critical event is based on an analyte level sensed in the human or wherein the critical event is an error that has occurred in the in vivo analyte sensor or the sensor interface application.

12. A mobile communication device, comprising:
a non-transitory memory on which a user downloadable sensor interface application and a user downloadable user interface application are stored;
an RF transceiver adapted to receive data from an in vivo analyte sensor; and
at least one processor communicatively coupled with the non-transitory memory and the RF transceiver, wherein the at least one processor is adapted to execute the user downloadable sensor interface application and adapted to:
process the received data with the user downloadable sensor interface application to generate data indicative of an analyte level of the human;
determine, with the user downloadable sensor interface application, whether the user downloadable user interface application is authorized by reference to a registration database;
grant, with the user downloadable sensor interface application to the user downloadable user interface application, if authorized, access to the data indicative of the analyte level of the human;
communicate the data indicative of the analyte level of the human from the user downloadable sensor interface application to the user downloadable user interface application, wherein the user downloadable sensor interface application and the user downloadable user interface application are both operating on the mobile communication device; and
cause display of the analyte level of the human on a display of the mobile communication device with the user interface application; and
if there is receipt of an indication, at the user downloadable sensor interface application, that access of the user downloadable user interface application to the data indicative of the analyte level of the human is to be removed, then remove access of the user downloadable user interface application to the data indicative of the analyte level of the human.

13. The mobile communication device of claim 12, wherein the user downloadable user interface application is a first user interface application adapted to cause display of the analyte level of the human on the display of the mobile communication device, and the user downloadable sensor interface application is adapted to communicate with a second user interface application adapted to cause display of the analyte level of the human on the display of the mobile communication device.

14. The mobile communication device of claim 13, wherein the at least one processor is further adapted to:
cause the capture of data from either the first user interface application or the second user interface application; and
provide the captured data to the other of the first or second user interface applications.

15. The mobile communication device of claim 12, wherein the at least one processor is further adapted to:
determine that a critical event has occurred; and
provide an indication to the user downloadable user interface application that the critical event has occurred.

16. The mobile communication device of claim 15, wherein the at least one processor is further adapted to:
if a confirmation was not received from the user downloadable user interface application that a notification of the critical event was provided to a user, then request that the user downloadable user interface application provide the notification to the user.

17. The mobile communication device of claim 16, wherein the at least one processor is further adapted to:
after the request that the user downloadable user interface application provide the notification, if a confirmation is not received from the user downloadable user interface application that the notification was provided, then disconnect the user downloadable user interface application from the user downloadable sensor interface application.

18. The mobile communication device of claim 16, wherein the at least one processor is further adapted to:
after the request that the user downloadable user interface application provide the notification, if a confirmation is not received from the user downloadable user interface application that the notification was provided, then log the critical event and cause an error message to be sent to a trusted computer system over the internet.

19. The mobile communication device of claim 15, wherein the at least one processor is further adapted to:
if a confirmation is not received from the user downloadable user interface application that a notification of the critical event was provided to a user, then provide the indication to the user downloadable user interface application that the critical event has occurred a second time.

20. The mobile communication device of claim 19, wherein the at least one processor is further adapted to:
after the indication is provided to the user downloadable user interface application a second time, if a confirmation is not received from the user downloadable user interface application that the notification was provided, then disconnect the user downloadable user interface application from the user downloadable sensor interface application.

21. The mobile communication device of claim 19, wherein the at least one processor is further adapted to:
after the indication is provided to the user downloadable user interface application a second time, if a confirmation is not received from the user downloadable user interface application that the notification was provided, then log the critical event and cause an error message to be sent to a trusted computer system over the internet.

22. The mobile communication device of claim 15, wherein the critical event is based on an analyte level sensed in the human or wherein the critical event is an error that has occurred in the in vivo analyte sensor or the user downloadable sensor interface application.

23. The method of claim 1, wherein the sensor interface application is provisioned by a first party associated with the manufacture of the in vivo analyte sensor and the user interface application is provisioned by a second party that is different from the first party.

24. The mobile communication device of claim 12, wherein the user downloadable sensor interface application is provisioned by a first party associated with the manufacture of the in vivo analyte sensor and the user downloadable user interface application is provisioned by a second party that is different from the first party.

25. The method of claim 1, further comprising the following step performed by the user interface application:
    causing display of a current analyte level of the human on the display of the mobile communication device based at least in part on a determination that a current data age window of the data indicative of the analyte level of the human has not expired.

26. The method of claim 1, wherein the sensor interface application does not cause display of the analyte level of the human on the display.

27. The mobile communication device of claim 12, wherein the user downloadable sensor interface application is adapted to not cause display of the analyte level of the human on the display.

28. The method of claim 1, wherein determining, by the sensor interface application, whether the user interface application is authorized comprises:
    sending information about the user interface application from the sensor interface application to a remote registration server;
    receiving an indication from the remote registration server whether the user interface application is approved for operation with the sensor interface application;
    generating and assigning a registration identifier, by the sensor interface application, for the user interface application if the indication indicates that the user interface application is approved for operation with the sensor interface application; and
    communicating the registration identifier to the user interface application.

* * * * *